(12) United States Patent
Ziv

(10) Patent No.: US 8,127,768 B2
(45) Date of Patent: Mar. 6, 2012

(54) APPARATUS FOR THE TREATMENT OF FEMININE PELVIC ORGAN PROLAPSE

(75) Inventor: Elan Ziv, Ramat-Gan (IL)

(73) Assignee: ConTIPI Ltd., Caesarea (IL)

( * ) Notice: Subject to any disclaimer, the term of this patent is extended or adjusted under 35 U.S.C. 154(b) by 627 days.

(21) Appl. No.: 10/593,367

(22) PCT Filed: Mar. 17, 2005

(86) PCT No.: PCT/IL2005/000303
§ 371 (c)(1),
(2), (4) Date: Dec. 10, 2007

(87) PCT Pub. No.: WO2005/087153
PCT Pub. Date: Sep. 22, 2005

(65) Prior Publication Data
US 2008/0149109 A1 Jun. 26, 2008

Related U.S. Application Data

(60) Provisional application No. 60/553,966, filed on Mar. 18, 2004, provisional application No. 60/553,965, filed on Mar. 18, 2004, provisional application No. 60/555,979, filed on Mar. 25, 2004, provisional application No. 60/602,636, filed on Aug. 19, 2004.

(51) Int. Cl.
*A61F 6/06* (2006.01)
*A61F 2/00* (2006.01)

(52) U.S. Cl. ............ 128/834; 128/830; 600/37; 600/38; 606/193

(58) Field of Classification Search .................. 128/830, 128/834–838, 898; 600/37, 38–41; 606/193, 606/197
See application file for complete search history.

(56) References Cited

U.S. PATENT DOCUMENTS
2,141,040 A * 12/1938 Holt ............................. 128/837
(Continued)

FOREIGN PATENT DOCUMENTS
DE 19816349 10/1999
(Continued)

OTHER PUBLICATIONS
Official Action Dated Apr. 29, 2010 From the US Patent and Trademark Office Re.: U.S. Appl. No. 10/598,872.
(Continued)

*Primary Examiner* — Patricia Bianco
*Assistant Examiner* — Keri J Nelson

(57) ABSTRACT

An apparatus for treating pelvic organ prolapse, comprising a main body adapted to provide pelvic organ support when inserted into a vagina; and, an applicator for inserting the main body into a vagina.

34 Claims, 20 Drawing Sheets

U.S. PATENT DOCUMENTS

| | | | | |
|---|---|---|---|---|
| 2,146,574 | A * | 2/1939 | Hay | 128/838 |
| 2,432,768 | A * | 12/1947 | Kurkjian | 128/835 |
| 2,938,519 | A | 5/1960 | Marco | |
| 3,138,159 | A | 6/1964 | Schmidt | |
| 3,646,929 | A | 3/1972 | Bonnar | |
| 3,789,828 | A | 2/1974 | Schulte | |
| 3,797,478 | A | 3/1974 | Walsh et al. | |
| 3,841,304 | A | 10/1974 | Jones | |
| 4,019,498 | A | 4/1977 | Hawtrey | |
| 4,019,499 | A | 4/1977 | Fitzgerald | |
| 4,139,006 | A | 2/1979 | Corey | |
| 4,212,301 | A | 7/1980 | Johnson | |
| 4,307,716 | A | 12/1981 | Davis | |
| 4,428,365 | A | 1/1984 | Hakky | |
| 4,457,299 | A | 7/1984 | Cornwell | |
| 4,553,533 | A | 11/1985 | Leighton | |
| 4,726,805 | A | 2/1988 | Sanders | |
| 4,823,814 | A | 4/1989 | Drogendijk et al. | |
| 4,846,784 | A | 7/1989 | Haber | |
| 4,850,963 | A | 7/1989 | Sparks et al. | |
| 4,920,986 | A | 5/1990 | Biswas | |
| 5,007,894 | A | 4/1991 | Enhorning | |
| 5,014,722 | A | 5/1991 | Bauer | |
| 5,036,867 | A | 8/1991 | Biswas | |
| 5,090,424 | A | 2/1992 | Simon et al. | |
| 5,224,494 | A | 7/1993 | Enhorning | |
| 5,336,208 | A | 8/1994 | Rosenbluth et al. | |
| 5,386,836 | A | 2/1995 | Biswas | |
| 5,417,226 | A | 5/1995 | Juma | |
| 5,483,976 | A | 1/1996 | McLaughlin et al. | |
| 5,603,685 | A | 2/1997 | Tutrone, Jr. | |
| 5,609,586 | A | 3/1997 | Zadini et al. | |
| 5,618,256 | A | 4/1997 | Reimer | |
| 5,659,934 | A | 8/1997 | Jessup et al. | |
| 5,671,755 | A | 9/1997 | Simon et al. | |
| 5,724,994 | A | 3/1998 | Simon et al. | |
| 5,771,899 | A | 6/1998 | Martelly et al. | |
| 5,785,640 | A | 7/1998 | Kresch | |
| 5,788,664 | A | 8/1998 | Scalise | |
| 5,795,346 | A | 8/1998 | Achter et al. | |
| 5,894,842 | A | 4/1999 | Rabin et al. | |
| 6,013,023 | A | 1/2000 | Klingenstein | |
| 6,090,038 | A | 7/2000 | Zunker et al. | |
| 6,090,098 | A | 7/2000 | Zunker et al. | |
| 6,142,928 | A | 11/2000 | Zunker et al. | |
| 6,158,435 | A | 12/2000 | Dorsey | |
| 6,189,535 | B1 | 2/2001 | Enhorning | |
| 6,216,698 | B1 | 4/2001 | Regula | |
| 6,413,206 | B2 | 7/2002 | Biswas | |
| 6,415,484 | B1 | 7/2002 | Moser | |
| 6,418,930 | B1 | 7/2002 | Fowler | |
| 6,458,072 | B1 | 10/2002 | Zunker | |
| 6,460,542 | B1 | 10/2002 | James | |
| 6,478,726 | B1 | 11/2002 | Zunker | |
| 6,503,190 | B1 | 1/2003 | Ulmsten et al. | |
| 6,558,370 | B2 | 5/2003 | Moser | |
| 6,645,136 | B1 | 11/2003 | Zunker et al. | |
| 6,676,594 | B1 | 1/2004 | Zunker et al. | |
| 6,679,831 | B1 | 1/2004 | Zunker et al. | |
| 6,739,340 | B1 | 5/2004 | Jensen et al. | |
| 6,770,025 | B2 | 8/2004 | Zunker | |
| 6,808,485 | B2 | 10/2004 | Zunker | |
| 7,036,511 | B2 | 5/2006 | Nissenkorn | |
| 7,717,892 | B2 | 5/2010 | Bartning et al. | |
| 2002/0068023 | A1 | 6/2002 | Davis | |
| 2002/0083949 | A1* | 7/2002 | James | 128/830 |
| 2002/0120243 | A1 | 8/2002 | Kraemer et al. | |
| 2002/0138035 | A1 | 9/2002 | Hull, Jr. | |
| 2002/0183711 | A1 | 12/2002 | Moser | |
| 2003/0149334 | A1 | 8/2003 | Ulmsten et al. | |
| 2003/0149392 | A1 | 8/2003 | Arnould | |
| 2004/0054252 | A1 | 3/2004 | Zunker | |
| 2004/0078013 | A1 | 4/2004 | Zunker et al. | |
| 2004/0084054 | A1* | 5/2004 | Kaseki et al. | 128/885 |
| 2004/0122285 | A1 | 6/2004 | Zunker | |
| 2004/0158122 | A1 | 8/2004 | Guerquin | |
| 2004/0199100 | A1 | 10/2004 | LeMay et al. | |
| 2007/0088189 | A1 | 4/2007 | Levy | |
| 2007/0203429 | A1 | 8/2007 | Ziv | |
| 2007/0244352 | A1 | 10/2007 | Ziv | |
| 2008/0281149 | A1 | 11/2008 | Sinai et al. | |
| 2009/0266367 | A1 | 10/2009 | Ziv et al. | |
| 2009/0283099 | A1 | 11/2009 | Harmanli | |

FOREIGN PATENT DOCUMENTS

| | | |
|---|---|---|
| EP | 0264258 | 4/1988 |
| EP | 0274762 | 7/1988 |
| EP | 0933069 | 8/1988 |
| EP | 0700669 | 3/1996 |
| EP | 0955024 | 11/1999 |
| EP | 1139962 | 5/2005 |
| FR | 2843700 | 2/2004 |
| GB | 1115727 | 5/1968 |
| GB | 2352181 | 1/2001 |
| GB | 2384436 | 7/2003 |
| JP | 06-133996 | 5/1994 |
| JP | 61-33996 | 5/1994 |
| JP | 09-501595 | 2/1997 |
| WO | WO 88/10106 | 12/1988 |
| WO | WO 89/09582 | 10/1989 |
| WO | WO 95/05790 | 3/1995 |
| WO | WO 96/01084 | 1/1996 |
| WO | WO 97/34550 | 9/1997 |
| WO | WO 00/36996 | 6/2000 |
| WO | WO 00/67662 | 11/2000 |
| WO | WO 02/26160 | 4/2002 |
| WO | WO 02/089704 | 11/2002 |
| WO | WO 03/047476 | 6/2003 |
| WO | WO 2004/000433 | 12/2003 |
| WO | WO 2004/103213 | 12/2004 |
| WO | WO 2005/087153 | 9/2005 |
| WO | WO 2005/087154 | 9/2005 |
| WO | WO 2006/097935 | 9/2006 |
| WO | WO 2008/010214 | 1/2008 |
| WO | WO 2008/079271 | 7/2008 |
| WO | WO 2008/152628 | 12/2008 |
| WO | WO 2009/044394 | 4/2009 |
| WO | WO 2009/130702 | 10/2009 |

OTHER PUBLICATIONS

Supplemental Notice of Allowability Dated Apr. 27, 2010 From the US Patent and Trademark Office Re.: U.S. Appl. No. 10/557,865.

Communication Relating to the Results of the Partial International Search Dated Aug. 18, 2009 From the International Searching Authority Re.: Application No. PCT/IL2009/000443.

Communication Under Rule 112 EPC Dated Oct. 22, 2007 From the European Patent Office Re.: Application No. 05718876.5.

European Search Report Under Rule 112 EPC Dated Dec. 27, 2007 From the European Patent Office Re.: Application No. 05718876.5.

International Preliminary Report on Patentability Dated Jul. 6, 2006 From the International Preliminary Examining Authority Re.: Application No. PCT/IL2005/000304.

International Search Report Dated Dec. 11, 2006 From the International Searching Authority Re.: Application No. PCT/IL06/00346.

International Search Report Dated Apr. 14, 2008 From the International Searching Authority Re.: Application No. PCT/IL2007/000893.

International Search Report Dated Sep. 23, 2005 From the International Searching Authority Re.: Application No. PCT/IL2005/000304.

Written Opinion Dated Dec. 11, 2006 From the International Searching Authority Re.: Application No. PCT/IL06/00346.

Written Opinion Dated Apr. 14, 2008 From the International Searching Authority Re.: Application No. PCT/IL2007/000893.

Written Opinion Dated Nov. 22, 2005 From the International Searching Authority Re.: Application No. PCT/IL2004/000433.

Written Opinion Dated Sep. 23, 2005 From the International Searching Authority Re.: Application No. PCT/IL2005/000304.

Communication Pursuant to Article 94(3) EPC Dated Mar. 23, 2010 From the European Patent Office Re.: Application No. 05718876.5.

International Preliminary Report on Patentability Dated Dec. 8, 2009 From the International Preliminary Examining Authority Re.: Application No. PCT/IL2008/001292.

International Preliminary Report on Patentability Dated Oct. 14, 2008 From the International Preliminary Examining Authority Re.: Application No. PCT/IL06/00346.
International Search Report and the Written Opinion Dated Oct. 26, 2005 From the International Searching Authority Re.: Application No. PCT/IL2005/000303.
Official Action Dated Oct. 15, 2009 From the US Patent and Trademark Office Re.: U.S. Appl. No. 10/557,865.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Written Opinion Dated May 23, 2006 From the International Preliminary Examining Authority Re.: Application No. PCT/IL2005/000303.
International Search Report Dated Oct. 24, 2008 From the International Searching Authority Re.: Application No. PCT/IL2008/000786.
Office Action Dated Sep. 1, 2008 From the Israeli Patent Office Re.: Application No. 156070 and Its Translation Into English.
Office Action Dated Sep. 1, 2008 From the Israeli Patent Office Re.: Application No. 157117 and Its Translation Into English.
Official Action Dated Sep. 5, 2008 From the US Patent and Trademark Office Re.: U.S. Appl. No. 10/557,865.
Written Opinion Dated Oct. 24, 2008 From the International Searching Authority Re.: Application No. PCT/IL2008/000786.
Examiner's Report Dated Dec. 9, 2009 From the Australian Government, IP Australia Re.: Application No. 2005221424.
International Preliminary Report on Patentability Dated Jul. 6, 2006 From the International Preliminary Examining Authority Re.: Application No. PCT/IL2005/000304.
International Preliminary Report on Patentability Dated Dec. 23, 2009 From the International Bureau of WIPO Re.: Application No. PCT/IL2008/000786.
International Search Report and the Written Opinion Dated Oct. 28, 2009 From the International Searching Authority Re.: Application No. PCT/IL2009/000443.
Notice of Allowance Dated Mar. 31, 2010 From the US Patent and Trademark Office Re.: U.S. Appl. No. 10/557,865.
Office Action Dated Sep. 1, 2008 From the Israeli Patent Office Re.: Application No. 156070 and Its Translation Into English.
Office Action Dated Jan. 18, 2010 From the Israel Patent Office Re.: Application No. 156070 and Its Translation Into English.
Official Action Dated Oct. 27, 2009 From the Federal Institute of Industrial and Intellectual Property, Patents and Trademarks, ROSPATENT, of the Russian Federation Re.: Application No. 2007138489 and Its Translation Into English.
Response Dated Mar. 15, 2010 to Official Action of Oct. 15, 2009 From the US Patent and Trademark Office Re.: U.S. Appl. No. 10/557,865.
Response Dated Feb. 22, 2010 to International Search Report and the Written Opinion of Oct. 28, 2009 From the International Searching Authority Re.: Application No. PCT/IL2009/000443.
Response Dated Dec. 27, 2009 to Official Action of Oct. 29, 2009 From the Federal Institute of Industrial and Intellectual Property, Patents and Trademarks, ROSPATENT, of the Russian Federation Re.: Application No. 2007138489.
Translation of Office Action Dated Jan. 19, 2010 From the State Intellectual Property Office of the People's Republic of China Re.: Application No. 200680017262.2.
Translation of Notification of Reasons of Rejection Dated Apr. 8, 2010 From the Japanese Patent Office Re.: Application No. 2007-503494.
Communication Pursuant to Article 94(3) EPC Dated Apr. 16, 2009 From the European Patent Office Re.: Application No. 05718876.5.
Communication Relating to the Results of the International Search Dated Dec. 7, 2007 From the International Searching Authority Re.: Application No. PCT/IL2007/000893.
Communication Relating to the Results of the Partial International Search Dated Jan. 12, 2009 From the International Searching Authority Re.: Application No. PCT/IL2008/001292.
International Preliminary Report on Patentability Dated Oct. 14, 2008 From the International Preliminary Examining Authority Re.: Application No. PCT/IL06/00346.
International Preliminary Report on Patentability Dated Jul. 24, 2006 From the International Preliminary Examining Authority Re.: Application No. PCT/IL2005/000303.
International Preliminary Report on Patentability Dated Jan. 29, 2009 From the International Bureau of WIPO Re.: Application No. PCT/IL2007/000893.
International Search Report Dated Mar. 25, 2009 From the International Searching Authority Re.: Application No. PCT/IL2008/001292.
Notification Dated Dec. 17, 2008 From the Russian Patent Office Re.: Application No. 2006136791 and Its Translation Into English.
Office Action Dated Jan. 9, 2009 From the State Intellectual Property Office of the People's Republic of China Re.: Application No. 200580016245.2 and Its Translation Into English.
Official Action Dated Mar. 6, 2009 From the US Patent and Trademark Office Re.: U.S. Appl. No. 10/557,865.
Official Action Dated Apr. 17, 2009 From the Patent Office of the Russian Federation Re.: Application No. 2006136791 and Its Translation Into English.
Official Action Dated Dec. 17, 2008 From the Patent Office of the Russian Federation Re.: Application No. 2006136791.
Written Opinion Dated Mar. 25, 2009 From the International Searching Authority Re.: Application No. PCT/IL2008/001292.
Communication Relating to the Results of the Partial International Search Dated Jan. 12, 2009 From the International Searching Authority Re.: Application No. PCT/IL2008/001292.
Notification Dated Dec. 17, 2008 From the Russian Patent Office Re.: Application No. 2006136791 and Its Translation Into English.
Office Action Dated Jan. 9, 2009 From the State Intellectual Property Office of the People's Republic of China Re.: Application No. 200580016245.2 and Its Translation Into English.
Official Action Dated Mar. 6, 2009 From the US Patent and Trademark Office Re.: U.S. Appl. No. 10/557,865.
Translation of Notification of Reasons for Rejection Dated Jun. 1, 2010 From the Japanese Patent Office Re. Application No. 2006-531002.
Response Dated Jun. 21, 2010 to Office Action of Jan. 29, 2010 From the State Intellectual Property Office of the People's Republic of China Re.: Application No. 200680017262.2.
Reponse Dated Jun. 29, 2010 to Official Action of Apr. 29, 2010 From the US Patent and Trademark Office Re.: U.S. Appl. No. 10/598,872.
Official Action Dated Jun. 11, 2010 From the Federal Institute of Industrial and Intellectual Property, Patents and Trademarks, ROSPATENT, of the Russian Federation Re.: Application No. 2010100368 and Its Summary Into English.
Letter After Telephone Conference Dated Jul. 5, 2010 From the International Searching Authority Re. Application No. PCT/IL2009/000443.
Communiction Pursuant to Article 94(3) EPC Dated Jul. 2, 2010 From the European Patent Office Re.: Application No. 05718877.3.
International Preliminary Report on Patentability Dated Jul. 15, 2010 From the International Preliminary Examining Authority Re.: Application No. PCT/IL2009/000443.
Official Action Dated Aug. 4, 2010 From the US Patent and Trademark Office Re.: U.S. Appl. No. 10/598,872.
Response Dated Aug. 1, 2010 to Notification of Reasons of Rejection Dated Apr. 8, 2010 From the Japanese Patent Office Re.: Application No. 2007-503494.
Response Dated Aug. 30, 2010 to Notification of Reasons for Rejection of Jun. 1, 2010 From the Japanese Patent Office Re. Application No. 2006-531002.
Response Dated Aug. 31, 2010 to Official Action of Aug. 4, 2010 From the US Patent and Trademark Office Re.: U.S. Appl. No. 10/598,872.
Official Action Dated Oct. 12, 2010 From the US Patent and Trademark Office Re.: U.S. Appl. No. 10/598,872.
Response Dated Jan. 17, 2011 to Examiner's Report of Dec. 15, 2010 From the Australian Government, IP Australia Re.: Application No. 2005221424.

Response Dated Jan. 12, 2011 to Examination Report of Oct. 13, 2010 From the Instituto Mexicano de la Propriedad Industrial Re. Application No. MX/a/2007/011339.
Response Dated Jan. 13, 2011 to Official Action of Oct. 12, 2010 From the US Patent and Trademark Office Re.: U.S. Appl. No. 10/598,872.
Notice of Acceptance Dated Feb. 2, 2011 From the Australian Government, IP Australia Re.: Application No. 2005221424.
Communication Pursuant to Article 94(3) EPC Dated Feb. 4, 2011 From the European Patent Office Re. Application No. 04734069.0.
Communication Relating to the Results of the Partial International Search Dated Mar. 3, 2011 From the International Searching Authority Re. Application No. PCT/IL2010/000985.
Communication Relating to the Results of the Partial International Search Dated Dec. 7, 2007 From the International Searching Authority Re.: Application No. PCT/IL2007/000893.
Examiner's Report Dated Dec. 15, 2010 From the Australian Government, IP Australia Re.: Application No. 2005221424.
Examiner's Report Dated Nov. 29, 2010 From the Australian Government, IP Australia Re. Application No. 2006224158.
Notification Dated Dec. 17, 2008 From the Patent Office of the Russian Federation Re.: Application No. 2006136791 and Its Translation Into English.
Notification of Reasons for Rejection Dated Feb. 18, 2011 From the Japanese Patent Office Re. Application No. 2007-503494 and Its Translation into English.
Official Action Dated Feb. 14, 2011 From the US Patent and Trademark Office Re.: U.S. Appl. No. 10/598,872.
Response Dated Nov. 3, 2010 to Communication Pursuant to Article 94(3) EPC of Jul. 2, 2010 From the European Patent Office Re. Application No. 057188877.3.
Response Dated Dec. 8, 2010 to Examiner's Report of Dec. 9, 2009 From the Australian Government, IP Australia Re.: Application No. 2005221424.
Response Dated Jan. 12, 2011 to Examination Report of Oct. 13, 2010 From the Instituto Mexicano de la Propriedad Industrial Re. Application No. MX/a/2007/011339.
Response Dated Nov. 16, 2010 to Office Action of Sep. 17, 2010 From the State Intellectual Property Office of the People's Republic of China Re.: Application No. 200680017262.2.
Response Dated Jan. 17, 2011 to Examiner's Report of Dec. 15, 2010 From the Australian Government, IP Australia Re.: Application No. 2005221424.
Response Dated Sep. 30, 2010 to Communication Pursuant to Article 94(3) EPC of Mar. 23, 2010 From the European Patent Office Re.: Application No. 05718876.5.
Translation of Notification of Reasons for Rejection Dated Dec. 24, 2010 From the Japanese Patent Office Re. Application No. 2007-503495.
Translation of Office Action Dated Sep. 17, 2010 From the State Intellectual Property Office of the People's Republic of China Re.: Application No. 200680017262.2.
Translation of Office Action Dated Jan. 29, 2010 From the State Intellectual Property Office of the Peoples Republic of China Re.: Application No. 200680017262.2.
Translation of Notification of Reasons for Rejection Dated Mar. 18, 2011 From the Japanese Patent Office Re. Application No. 2006-531002.

Office Action Dated Apr. 5, 2011 From the Israel Patent Office Re.: Application No. 156070 and Its Translation Into English.
Response Dated Mar. 10, 2011 to Notification of Reasons for Rejection of Dec. 24, 2010 From the Japanese Patent Office Re. Application No. 2007-503495.
Examination Report Dated Mar. 31, 2011 From the Instituto Mexicano de la Propriedad Industrial Re. Application No. MX/a/2007/011339.
International Search Report and the Written Opinion Dated May 9, 2011 From the International Searching Authority Re. Application No. PCT/IL2010/000985.
Translation of Office Action Dated Apr. 29, 2011 From the State Intellectual Property Office of the People's Republic of China Re.: Application No. 200680017262.2.
Communication Under Rule 71(3) EPC Dated May 27, 2011 From the European Patent Office Re. Application No. 09735573.9.
Response Dated Jun. 1, 2011 to Notification of Reasons for Rejection of Mar. 18, 2011 From the Japanese Patent Office Re. Application No. 2006-531002.
Response Dated Jun. 14, 2011 to Official Action of Feb. 14, 2011 From the US Patent and Trademark Office Re.: U.S. Appl. No. 10/598,872.
Response Dated May 29, 2011 to Communication Pursuant to Article 94(3) EPC of Feb. 4, 2011 From the European Patent Office Re. Application No. 04734069.0.
Response Dated Jun. 5, 2011 to the Communication Pursuant to Article 94(3) EPC of Feb. 4, 2011 From the European Patent Office Re. Application No. 05734069.0.
Response Dated Aug. 7, 2011 to Office Action of Apr. 5, 2011 From the Israel Patent Office Re.: Application No. 156070.
Response Dated Aug. 10, 2011 to Official Action of May 31, 2011 From the US Patent and Trademark Office Re. U.S. Appl. No. 12/417,011.
Official Action Dated May 31, 2011 From the US Patent and Trademark Office Re. U.S. Appl. No. 12/417,011.
Response Dated Jun. 20, 2011 to Office Action of Dec. 21, 2010 From the State Intellectual Property Office of the People's Republic of China Re. Application No. 200780033622.2.
Translation of Office Action Dated Dec. 21, 2010 From the State Intellectual Property Office of the People's Republic of China Re. Application No. 200780033622.2.
Response Dated Jun. 29, 2011 to Office Action of Apr. 29, 2011 From the State Intellectual Property Office of the People's Republic of China Re.: Application No. 200680017262.2.
Office Action Dated Jul. 24, 2011 From the Israel Patent Office Re. Application No. 176883 and Its Translation Into English.
Response Dated Aug. 11, 2011 to Examination Report of Mar. 31, 2011 From the Instituto Mexicano de la Propriedad Industrial Re. Application No. MX/a/2007/011339.
Requisition by the Examiner Dated Aug. 29, 2011 From the Canadian Intellectual Property Office Re. Application No. 2,560,877.
Examination Report Dated Oct. 13, 2010 From the Instituto Mexican de la Propriedad Industrial Re. Application No. MX/a/2007/011339 and Its Summary in English.
Translation of Decision for Rejection Dated Jun. 9, 2011 From the Japanese Patent Office Re. Application No. 2007-503495.
Official Action Dated Oct. 14, 2011 From the US Patent and Trademark Office Re. U.S. Appl. No. 12/417,011.

* cited by examiner

APPARATUS FOR THE TREATMENT OF FEMININE PELVIC ORGAN PROLAPSE

RELATED APPLICATIONS

The present application is a US National Phase of PCT Application No. PCT/IL2005/000303, filed on Mar. 17, 2005. The present application also claims the benefit under 35 USC 119(e) of U.S. Provisional Application No. 60/553,965 filed on Mar. 18, 2004, U.S. Provisional Application No. 60/553,966 filed on Mar. 18, 2004, U.S. Provisional Application No. 60/555,979 filed on Mar. 25, 2004, and U.S. Provisional Application No. 60/602,636 filed on Aug. 19, 2004, the disclosures of which are herein incorporated by reference.

FIELD OF INVENTION

The present invention relates generally to the field of treatment and prevention of pelvic organ prolapse in female patients. For example, a specially shaped vaginal device that is inserted and removed by the patient is provided.

BACKGROUND OF THE INVENTION

Pelvic organ prolapse ("POP") is defined as a condition in which vaginal wall support is lost, and various pelvic organs prolapse into the vagina. This is a very troublesome condition, though in most cases it is not a dangerous one. POP might appear alone or in combination with urinary stress incontinence.

Prolapse of adjacent organs into the vagina is quite common, in variable degrees. The reasons for such a prolapse are mainly damage to the endopelvic fascia which surrounds the organs and keeps them in the right position, pelvic floor muscular damage, and/or neural damage. There might also be a change within the collagen composition, thereby causing a weaker pelvic floor. According to an older classification system, prolapse may be divided into five categories depending on the organ that is sagging down (urethra, bladder, uterus, rectum and the pouch of Douglas), and into three grades according to the amount of descent (within the vagina, at the entrance to the vagina, protruding out of the vagina). There might be a combination of various organs prolapse at the same time, with different levels of descent. The newer classification (POP-Q) takes into account other factors, such as location of the prolapse and the distance from the entrance of the vagina.

Prolapse of the urethra, named urethrocele, is one of the several possibilities for pelvic organ prolapse around the vagina. The most frequent prolapse is of the bladder, named cystocele, as a result of its weight. Prolapse of posterior fornix, with bowl inside is called enterocele, and prolapse of the posterior vaginal wall with the rectum in it is termed rectocele. When the ligaments that hold the uterus in place weaken, a uterine descent occurs. In cases where the uterus has been removed, and the vagina is dome shaped, a vault prolapse may occur.

Referring now to FIG. 1A, an anatomical front view of a vagina 100 is depicted. The sidewalls have thin longitudinal and circular muscles 108, externally wrapped by a pelvic fascia 110. It has been determined that the pelvic fascia 110 tends to become weakened, stretched and attenuated over time and as a result of various stresses, such as childbirth. Such weakening of the pelvic fascia allows for sagging and thus, prolapses of different pelvic organs into and through the vagina 100. The inside circumference of the vagina 100 is covered with mucosa 106.

The vaginal cavity is almost always deformed by prolapse when the anterior wall 112 collapses, or is too weak to hold. Often, the bladder's weight causes the anterior wall 112 to collapse and occlude the vaginal lumen from above. On the other hand, the posterior wall 114 can be stressed by the bowel. The conglomeration of these stresses can result in an occlusion of the vaginal lumen shaped like a letter "H", depicted in FIG. 1B.

FIG. 1C is an illustration of the vaginal shape from a side view. It can be seen that vaginal diameters are not constant along the vaginal axis. Lateral diameter is usually shorter closer to the entrance 118, but gradually becomes longer internally 116. The same applies for the antero-posterior diameter. The vaginal diameter close to the entrance is typically shorter than the vaginal diameter behind the perineal body. As a generalization, the vagina may be looked at as a funnel shaped organ.

There are certain defined organs in direct contact with the vagina or within short proximity, as depicted in FIG. 1D. The bladder 136 is a hollow, sack-like organ, in which the urine is accumulated prior to it's expulsion outside the body through the urethra 142. The bladder is located behind the pubic bone 138 and rests on the middle third of the vagina. The urethra is a short muscular pipe, 25-35 mms in length, in direct contact with the bladder at the bladder neck 140 resting on the lower third of the anterior vaginal wall, in direct contact with the pubic bone. The uterus 130 is a pear shaped organ that has a lower part, the cervix 132 which protrudes into the dome of the vagina. The body of the uterus is an abdominal organ, which, in most cases bends forward on the bladder. The cervix, while protruding into the vagina creates 4 fornices—2 laterals which are of the same dimensions, one smaller anterior 134, and one posterior 122, which is actually behind the cervix 132. The posterior fornix has direct contact with the pouch of Douglas 120 which is the deepest part of the abdominal cavity, on top of the vagina. The posterior surface of the vagina is in contact with the rectum 124, until the area where a thick muscular body, the perineal body which is part of the pelvic floor and the sphincter of the anus 128.

At present there are two ways of dealing with Pelvic Organ Prolapse. The first method for treatment involves surgery, which can be vaginal or abdominal. Surgical intervention is typically undesirable due to cost, pain and suffering to the patient and the possibility that even surgery will fail to be effective. Efforts to avoid surgical procedures have resulted in the development of a number of non-surgical vaginal devices, inserted into the vagina by the surgeon or the patient. Therefore, the second method of treatment requires the use of vaginal devices (pessaries) that are inserted into the vagina and mechanically reduce the prolapse by pushing the vaginal walls aside and upwards. Vaginal devices are well known for their tremendous diversity in shapes and sizes.

Some of these devices tend to block all flow of urine from the bladder. Therefore, when a patient needs to urinate, the device must be removed from the vagina or must be collapsed to remove the pressure applied against the bladder neck. Trying to solve this problem, vaginal devices were developed in special shapes that do not completely block the bladder neck, so that the patient may urinate with the device in place. These devices, however, are generally large and intrusive and, therefore, are uncomfortable to insert, wear and remove, with low patient satisfaction and compliance. They are also relatively expensive, and therefore designed to be reusable. Various pessary devices have been designed to treat prolapse in women, for example, U.S. Pat. No. 6,189,535; U.S. Pat. No. 6,158,435; U.S. Pat. No. 5,894,842; U.S. Pat. No. 5,771,899;

U.S. Pat. No. 5,611,768; U.S. Pat. No. 4,823,814; and GB 19124034, the disclosures of which are herein incorporated by reference.

An example of how to overcome some of the above limitations in the prior art would be to provide a flexible pessary which assumes a low profile for insertion and removal, but which assumes a larger profile while treating pelvic organ prolapse.

Another example of how to overcome some of the above limitations in the prior art would be to provide a pessary that does not apply direct pressure to the urethra, thereby restricting a woman's ordinary urinary function.

SUMMARY OF THE INVENTION

An aspect of some embodiments of the invention relates to a device for the treatment of female pelvic organ prolapse which is non-planar. In an exemplary embodiment of the invention, a device is provided in which the non-planar aspect of the device is not preset prior to insertion into a vagina. Optionally, the device is non-planar to the extent that the vaginal walls are not stressed substantially in more than one axis.

An aspect of some embodiments of the invention relates to a thin device for treating feminine prolapse which is easy and comfortable to insert. Optionally, the device is constructed of a sufficiently flexible material to allow a collapsed, low-profile device to be inserted, which then assumes an operative shape different from the insertion shape. In some embodiments of the invention, the device is flexible at at least three hinged areas along the device. In some embodiments of the invention, the device is inserted using an applicator. Optionally, the device and/or the applicator are disposable. Optionally, the device is inserted without regard to the applicator's rotational orientation about its longer axis.

An aspect of some embodiments of the invention relates to a device for treating feminine prolapse which is provided with a device displacer to allow for easy removal of the device. Optionally, the device is thin. Optionally, the device is inserted into a vagina using an applicator. Optionally, the device displacer is a string. In some embodiments of the invention, the device is inserted already attached to the device displacer which remains attached to the device at least until removal of the device from the vagina.

An aspect of some embodiments of the invention relates to a device for treating feminine prolapse which includes an anchoring body. In an exemplary embodiment of the invention, the anchoring body provides for preventing unwanted movement of the device. Optionally, the anchoring body provides additional structure for preventing unwanted movement of the device. Optionally, the anchoring body is selectably attached to the device's main body to allow for easy and comfortable removal. In an exemplary embodiment of the invention, the anchoring body is removably affixed to the main ring at two indentations on the inner circumference of the main ring. Optionally, the indentations give way under the stress of a removal force, altering the shape of the device and allowing for easier removal. In some embodiments of the invention, the anchoring body can prevent the device from falling out while allowing the device to be more comfortable to the wearer. Optionally, the anchoring support enhances the efficacy of the device by encouraging forces to act in a trans-axial direction (defining an axial direction along the long axis of the vagina). Optionally, the anchoring body is ring shaped. In some embodiments of the invention, the anchoring body is used for other purposes besides anchoring a prolapse treatment device. For example, the anchoring body can be used for treatment of incontinence. Optionally, the anchoring body is used to treat prolapse conditions in addition to the main body of the prolapse treatment device.

An aspect of some embodiments of the invention relates to a device for treating feminine prolapse which is provided with variable rigidity depending on the needs of the patient. Additionally or alternatively, the variable rigidity attribute is used as a facilitator for insertion and removal. Optionally, the variably rigid device is provided with a fluid reservoir.

An aspect of some embodiments of the invention relates to an applicator for inserting a prolapse treatment device which is provided with a stopper. The stopper is located on the applicator such that by advancing the applicator into the vagina up to the stopper, the deployment of a device within the applicator will be at an appropriate depth for rendering effective treatment. Optionally, the stopper can be provided with selectable positions corresponding to different sized women, for personalization.

There is thus provided an apparatus for treating pelvic organ prolapse, comprising: a main body adapted to provide pelvic organ support when inserted into a vagina; and, an applicator for inserting said main body into a vagina. Optionally, said main body is non-planar, extending along three axes. In an exemplary embodiment of the invention, the apparatus further comprises a device displacer. In an exemplary embodiment of the invention, the apparatus further comprises a soft external layer located on at least a portion of said main body, said soft external layer adapted to enhance comfort. Alternatively or additionally, the apparatus further comprises a soft external layer located on at least a portion of said main body, said soft external layer adapted to prevent necrosis. Optionally, said apparatus is adapted to be flexible in response to force applied on said apparatus while in said vagina and during removal from said vagina. Optionally, the apparatus is disposable. In an exemplary embodiment of the invention, said apparatus is configured to not directly compress a urethra upon said insertion There is thus provided an apparatus for treating pelvic organ prolapse, comprising: a main body adapted to provide pelvic organ support when inserted into a vagina; and, an anchoring body, wherein said anchoring body is selectively affixed to said main body. Optionally, said main body is non-planar, extending along three axes. In an exemplary embodiment of the invention, the apparatus further comprises a device displacer. In an exemplary embodiment of the invention, the apparatus further comprises a soft external layer located on at least a portion of said main body. Optionally, said apparatus is adapted to be flexible in response to force applied on said apparatus while in said vagina and during removal from said vagina. Optionally, the apparatus is disposable. In an exemplary embodiment of the invention, said main body is deformable upon the application of a removal force towards a vaginal opening. In an exemplary embodiment of the invention, the apparatus further comprises an applicator adapted for insertion of said apparatus. Optionally, said anchoring body is ring shaped. Optionally, said anchoring body is ovoid. Alternatively or additionally, said anchoring body is multi-sided.

There is thus provided an apparatus for treating pelvic organ prolapse, comprising: a thin main body adapted to provide pelvic organ support when inserted into a vagina, which main body is deformable at at least three points thereon. Optionally, said main body is non-planar, extending along three axes. In an exemplary embodiment of the invention, the apparatus further comprises a device displacer adapted to impart movement to said apparatus. In an exemplary embodiment of the invention, the apparatus further comprises a soft external layer located on at least a portion of said main body, said soft external layer adapted to prevent necrosis. Optionally, said apparatus is adapted to be flexible in response to force applied on said apparatus while in said vagina and during removal from said vagina. Optionally, the apparatus is disposable. Optionally, said apparatus does not directly compress a urethra upon said insertion.

In an exemplary embodiment of the invention, an apparatus is provided wherein said main body is provided with a hollow lumen, and further comprising: a flexible tube, wherein said tube is attached to said main body and provided with a hollow lumen in fluid contact with said main body hollow lumen; a non-compressible fluid located within the lumen proscribed by said tube and main body; and, a blocking mechanism, wherein said blocking mechanism is slidably located on said tube thereby constraining said non-compressible fluid within said lumen. In an exemplary embodiment of the invention, the apparatus further comprises additional reservoir space, increasing the volume of the lumen proscribed by said tube and main body. In an exemplary embodiment of the invention, the apparatus further comprises an applicator used for insertion of said apparatus.

There is thus provided a method of treating pelvic organ prolapse, comprising: inserting into a vagina an apparatus for treating pelvic organ prolapse; and, positioning said apparatus within said vagina wherein said apparatus exhibits a non-planar configuration after said insertion. Optionally, inserting is facilitated by using an applicator. In an exemplary embodiment of the invention, the apparatus further comprises removing said apparatus from said vagina. Optionally, said removal is facilitated by a device displacer adapted to impart movement to said apparatus. In an exemplary embodiment of the invention, the apparatus further comprises disposing of said apparatus. Optionally, said positioning does not apply direct pressure to a urethra

BRIEF DESCRIPTION OF THE FIGURES

Non-limiting embodiments of the invention will be described with reference to the following description of exemplary embodiments, in conjunction with the figures. The figures are generally not shown to scale and any measurements are only meant to be exemplary and not necessarily limiting. In the figures, identical structures, elements or parts which appear in more than one figure are preferably labeled with a same or similar number in all the figures in which they appear, in which.

DETAILED DESCRIPTION OF EXEMPLARY EMBODIMENTS

A Prolapse Treatment Device

Figure 1A:
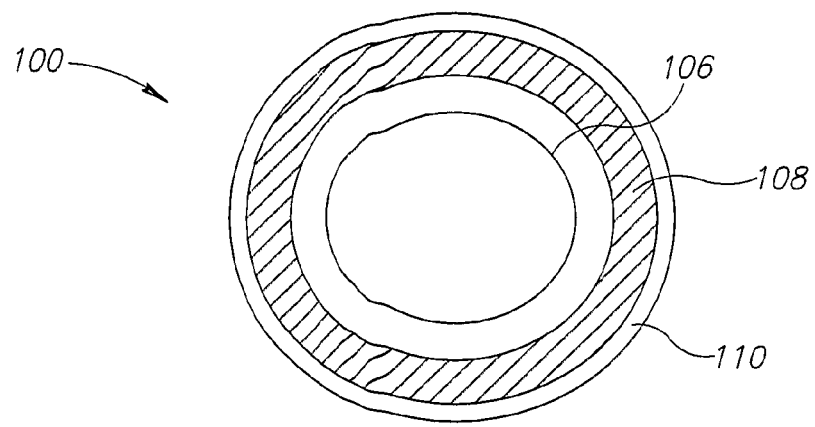
FIG. 1A is an anatomical front view of the vagina.
Figure 1B:
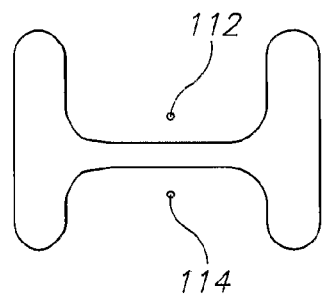
FIG. 1B is a view of the vagina when being compressed by the bladder from above and the bowels from below.
Figure 1C:
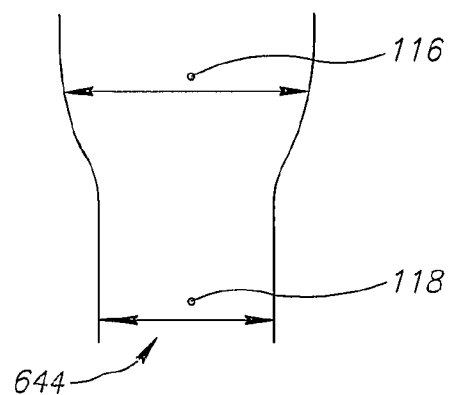
FIG. 1C is a side view of the vaginal shape.
Figure 1D:
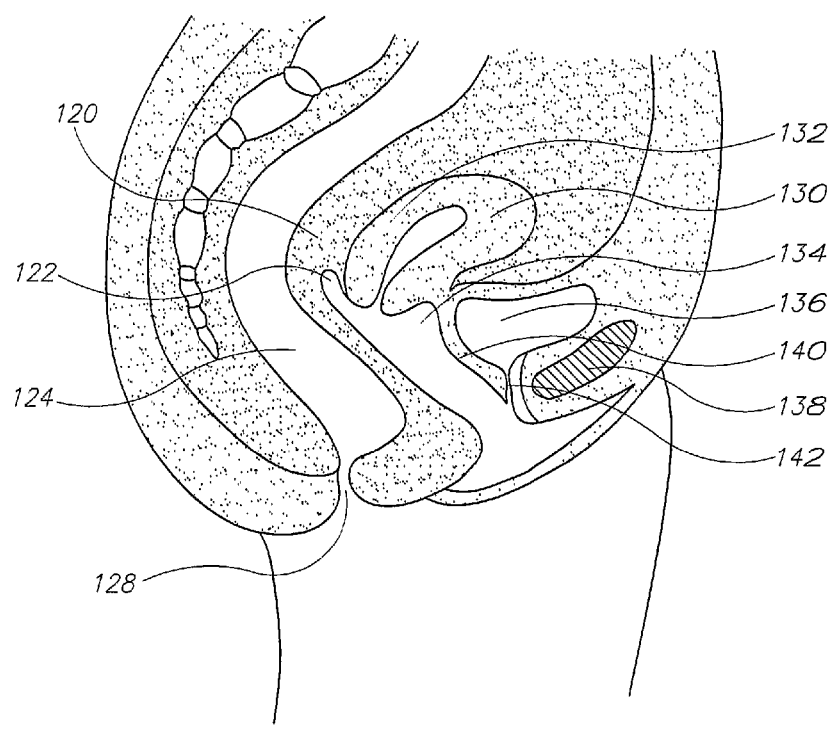
FIG. 1D is an illustration of the female pelvic region.
Figure 2A:
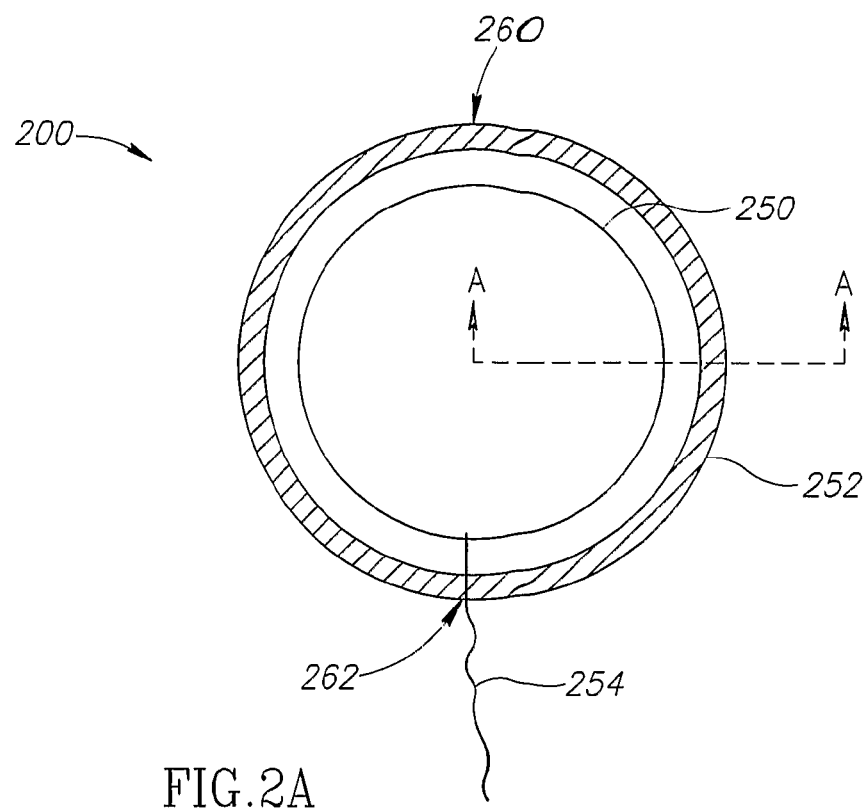
FIG. 2A is a top view of a prolapse treating device in accordance with an exemplary embodiment of the invention.
Figure 4A:
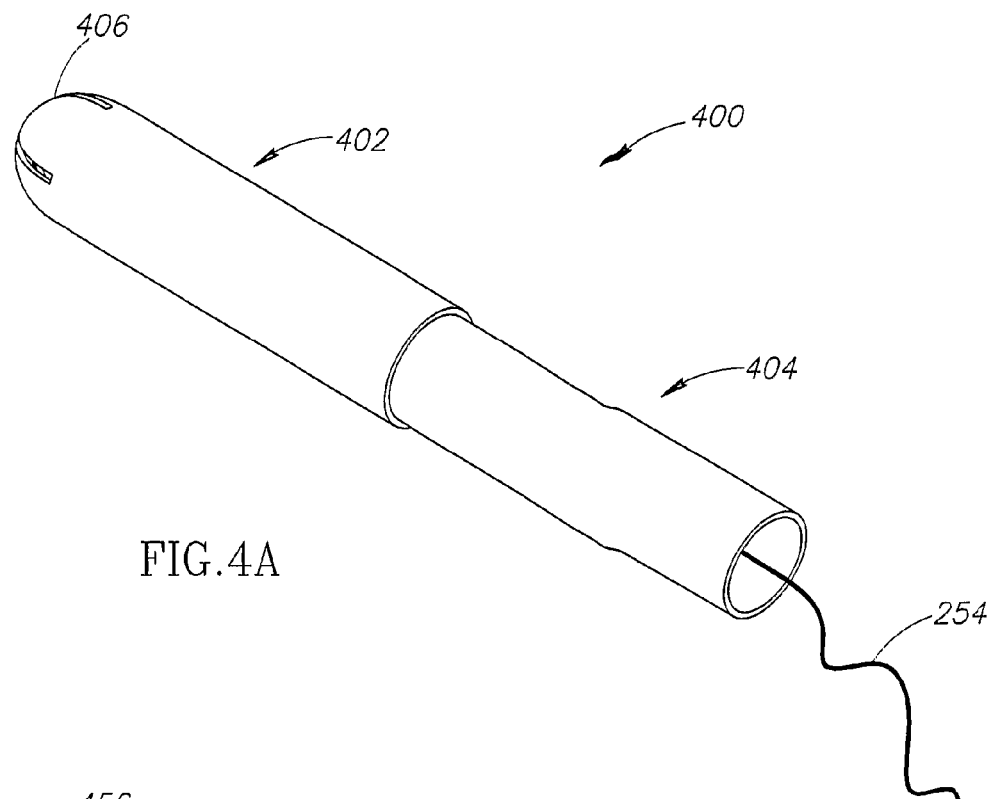
FIG. 4A is a perspective view of an applicator in accordance with an exemplary embodiment of the invention.
Figure 4B:
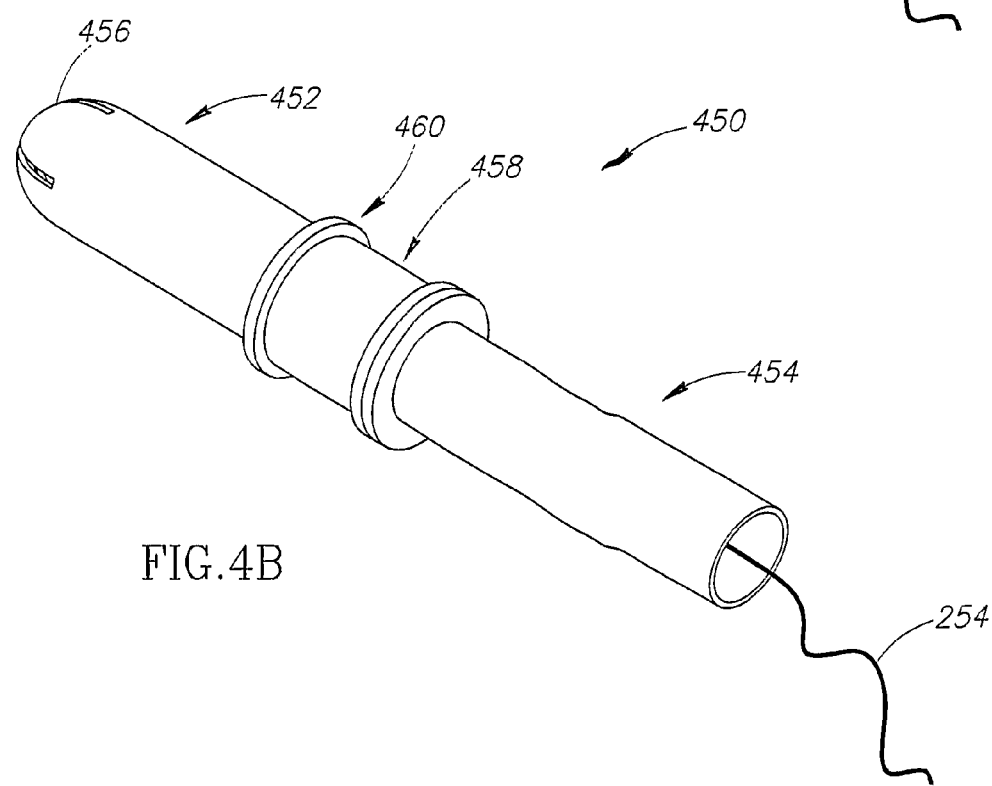
FIG. 4B is a perspective view of an applicator in accordance with an exemplary embodiment of the invention.

The vagina 100 is a hollow organ with multiple shapes and diameters at different depths. In an exemplary embodiment of the invention, device 200 is provided for the treatment of pelvic organ prolapse in females. FIG. 2A is a top view of device 200 in accordance with an embodiment of the invention. In this embodiment of the invention, device 200 has a main body 250 which appears to be a circular ring from a top view, although in some exemplary embodiments of device 200 a prolapse treatment device is provided which is oblong, multi-sided, star shaped, or ovoid. In an exemplary embodiment of the invention, device 200 is inserted into the vagina such that a distal end 260 is located substantially opposite the vaginal opening from device 200. Correspondingly, the proximal end 262 of device 200 is located nearer to the vaginal opening and device displacer 254. In an exemplary embodiment of the invention, device 200 is inserted such that a direct pressure is not exerted on the urethra by device 200. Optionally, main body 250 is made of elastic materials such as silicon and/or polyurethane. Usage of a flexible, optionally elastic, material gives the device the ability to be folded into an applicator, such as depicted in FIG. 4A or 4B, and to be pushed out easily within a small space and into the vagina. Optionally, the device is foldable at at least three different points. Optionally, the device is foldable along at least two axes.

Figure 2B:
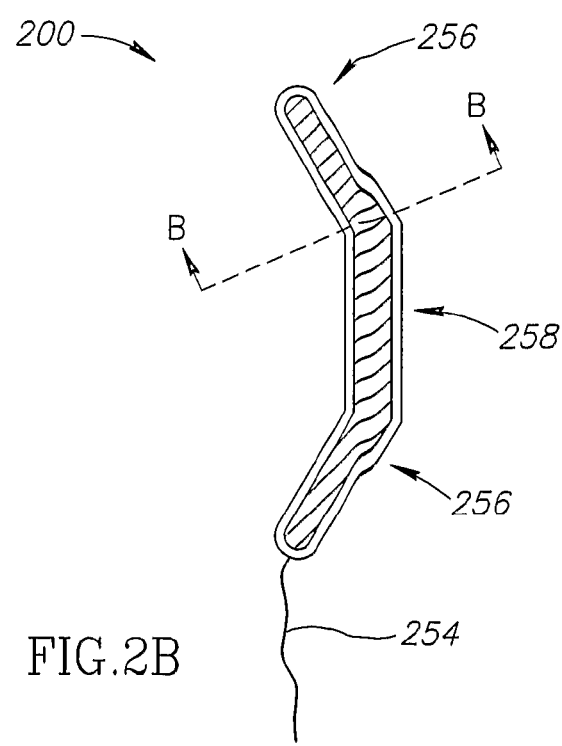
FIG. 2B is a profile view of a prolapse treating device in accordance with an exemplary embodiment of the invention.

FIG. 2B shows device 200 from the side in accordance with an exemplary embodiment of the invention. From this view, it can be seen that device 200 is not a planar ring, but instead has optional mirror image upturned portions 256 at each extremity, the device 200 is non-planar. By non-planar, it is meant that in addition to an x-axis which extends laterally across the vaginal lumen, and a y-axis which extends from the vaginal opening towards the uterus along, the x and y axes defining a plane, the device also extends in a z-axis extending from the vaginal floor towards the urethra. It should be noted that while device 200 has a height dimension in the z-axis, this is not what is meant when describing device 200 as non-planar. Exemplary portions of device 200, such as upturned portions 256, extend into the z-axis more than just as a function of height, this extension is non-planar. Optionally, upturned portions 256 are not angled to the same degree. Optionally, no portion or only one portion is angled with respect to the "flat" segment 258 of device 200. One disadvantage of some prior art devices is related to their potential for becoming dislodged while in situ, to the point that they fall out of the vagina. It has been determined that having upturned portions at the extremities of device 200 helps prevent the device from becoming dislodged and from falling out. Having a multi-planar device 200 requires more convoluted motion of device 200 in order to fall out than with just a single planar device. In some embodiments of the invention, a membrane is provided which occludes or substantially occludes the otherwise open internal area of device 200.

From this perspective it can also be seen that device 200 is relatively thin. That is, relative to the length of device 200, which can be defined as the dimension extending from proximal end 262 to distal end 260, its height, which can be defined as the dimension across which cross-sectional indicator line B-B extends is relatively small. In some embodiments of the invention, the height is less than one third of the length of device 200. Optionally, the ratio of height to length is one quarter. In some embodiments of the invention, the ratio of height to length is one fifth. The thin nature of device 200 allows for the collapsible quality which lends itself to storage in an applicator, easy insertion and removal, no significant blockage of vaginal fluid flow, and material cost savings.

In some embodiments of the invention, device 200 can be provided with varying degrees of stiffness along its length. In an exemplary embodiment, the unstressed device is substantially one planar. However, upon insertion into the vagina, where the vaginal walls exert pressure on device 200, the varying stiffness property of device 200 causes a pre-defined non-planar shape to be created. Using device 200 pictured in FIGS. 2A-C as an example, device 200 can be provided with less stiff sections equally spaced from a central axis of device 200 which when device is inserted into the vagina and pressure is exerted on device 200, creates the slightly upturned "wings" illustrated in FIG. 2B.

Figure 3A:
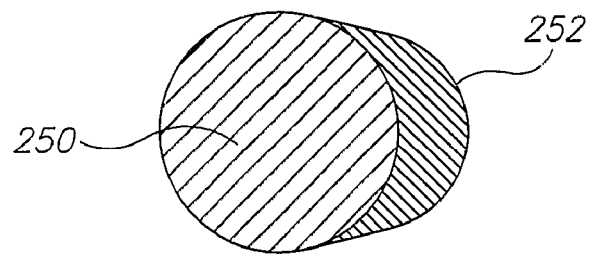
FIG. 3A is a cutaway view along line A-A of FIG. 2A in accordance with an exemplary embodiment of the invention.
Figure 3B:
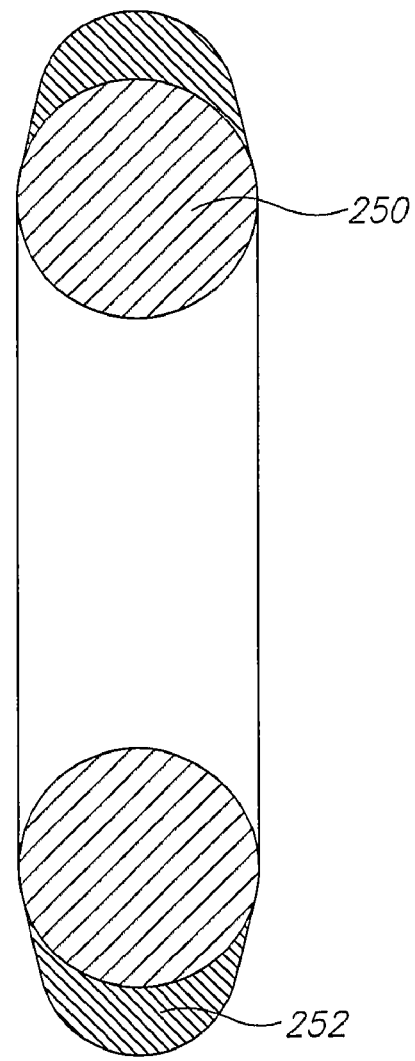
FIG. 3B is a cutaway view along line B-B of FIG. 2B in accordance with an exemplary embodiment of the invention.

In some embodiments of the invention, main body 250 is at least partially covered by an external soft layer 252. FIGS. 3A and B show cross-sectional views of device 200 which indicate the relative configuration of main body 250 and external soft layer 252. Optionally, the external soft layer is made of a material such as sponge rubber. Optionally, the external layer 252 is 5 mm or less in thickness. Usage of a soft material as external layer 252 to coat main body 250, reduces pressure exerted by device 200 on the vaginal wall and makes it much more comfortable to wear. In an exemplary embodiment of the invention, the external layer 252 is soft enough to make device 200 comfortable to wear. In an exemplary embodiment of the invention, the external layer 252 is soft enough to prevent necrosis during usage. In addition to comfort, reduction of the pressure exerted by device 200 on the sidewalls of the vagina reduces the chance of pressure-induced necrosis of the surrounding tissue. Pressure necrosis is less likely to happen because as the pressure applied to the sidewalls is reduced, blood flow within the vaginal walls is increased. An additional advantage for using some spongy external layer 252 materials is that they create between device 200 and the walls of the vagina, assisting with prevention of unwanted movement, including expulsion of the device. In some exemplary embodiments of the invention, spongy layer 252 is thicker or thinner than depicted in the FIGS. 3A and B. For example, the layer can be up to 5 mm thick. Optionally, the degree of coverage of main body 250 by external spongy layer 252 is more or less that depicted in the Figures. Optionally, the thickness and/or coverage by spongy layer 252 of main body 250 vary along the outer circumference of main body 250. In some embodiments of the invention, the cross-section of device 200 is not circular.

In an exemplary embodiment of the invention, device 200 is intended to be inserted into vagina 100 with an applicator, such as depicted in FIG. 4A or 4B, much like the insertion of a regular menstrual tampon. Insertion of the prolapse treating device 200 does not have to be precise with respect to the rotational angle of the applicator (and thus the device) to the vaginal opening 644. After insertion, the device expands significantly into its predefined shape and size, thereby exerting a predefined appropriate pressure on both lateral vaginal walls, pushing them aside. The apex of the vagina is pushed upwards at the same time due to the increased tightness of the vaginal walls caused by expanded device 200. As the woman moves (e.g. walks), device 200 will naturally settle into the appropriate rotational position for prolapse treatment in accordance with an exemplary embodiment of the invention. As device 200 expands into its predefined shape, an embodiment of which is depicted in FIG. 2A, the device stretches the anterior and posterior vaginal walls which provide additional strength and support against prolapse. In some exemplary embodiments of the invention, device 200 not only stretches the vaginal walls for additional strength, but because the device is non-planar, also optionally physically supports the prolapsing organs. The shape of the prolapse treatment device 200 is also designed to allow fluid flow out of the vagina. In some exemplary embodiments of the invention, fluid flow is allowed out of the vagina because the urethra is not substantially interfered with. The device 200 is aligned within the vagina such that a contact point between device 200 and the vaginal wall is not located on urethra 142. This relationship allows substantially unobstructed urinary function. In some exemplary embodiments, device 200 does not entirely occlude the vaginal lumen, and therefore, vaginal secretions and/or other fluids can exit from the vaginal opening. Optionally, the device is disposable. In other embodiments of the invention, the device is reusable and is sterilized between uses. Optionally the device is constructed of silicone or polyurethane.

Referring now to FIG. 4A, an applicator 400 is shown in accordance with an exemplary embodiment of the invention. It can be seen in the Figure that applicator 400 has a distal end 402, and a proximal end 404. In an exemplary embodiment of the invention, distal end 402 is provided with an exit 406 which is closed prior to use. In some embodiments of the invention, distal end 402 has exit 406 that is a slotted dome and the portions of distal end 402 which are located between the slots are deformable. Optionally, distal end 402 is scored to provide exit 406. Optionally, exit 206 is flower petal-like, provided with multiple opening "petals". However, upon application of pressure towards distal end 402 using proximal end 404 like a plunger, exit 406 opens and the prolapse treating device 200 located within exits applicator 400 and deploys in the vagina. Once device 200 is deployed, the empty applicator, consisting of distal end 402 and proximal end 404, is removed from the vagina. A device displacer 254, such as a string, optionally extends out of the open end of proximal end 404 and is attached to the prolapse treating device. The string remains attached to the prolapse treating device after applicator 400 is removed. Insertion is shown in detail in FIG. 6A. In some embodiments of the invention, applicator 400 is marked indicating the orientation of device 200 therein, should a specific device rotational angle with respect to the vagina be desired.

An exemplary embodiment of an applicator 450 is depicted in FIG. 4B. While applicator 450 is equipped with a proximal end 454, a distal end 452 and an exit 456, as with applicator 400, this embodiment additionally includes a stopper 458 which is positioned along applicator 450 such that when stopper 458 is grasped by a user upon insertion and applicator 450 is advanced into the vagina up to the distal lip 460 of stopper 458, deployment of a device located within applicator 450 is at an appropriate depth within the vagina to render effective treatment. Deployment of a device using this embodiment of an applicator is carried out in a manner similar to that described above, with the addition of using stopper 458 for convenient depth measurement. Optionally, the stopper can be provided with selectable positions corresponding to different sized women, for personalization In some embodiments of the invention, an applicator is used which conveniently positions a prolapse treatment device for insertion into a vagina. For example, any of the devices described herein can be positioned on or in an applicator in a collapsed and/or folded configuration ready to be inserted into a vagina. In an exemplary embodiment of the invention, the device would be inserted into the vagina using the applicator, and then would be allowed to spring into an expanded shape by releasing the mechanism holding the device in a collapsed configuration. In an exemplary embodiment of the invention, a releasable knot is tied around the device using the device displacer, the knot being released once the device is inserted into the vagina and the device displacer being located in an accessible place so that the device displacer can be used for removal of the device.

Figure 5A:
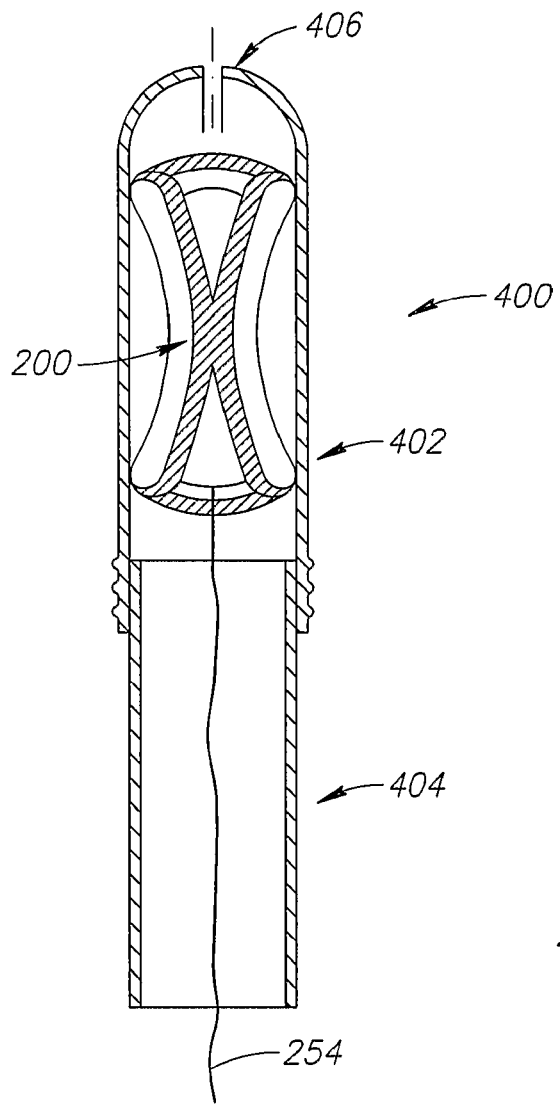
FIG. 5A is cutaway view of the device within the applicator in accordance with an exemplary embodiment of the invention.
Figure 5B:
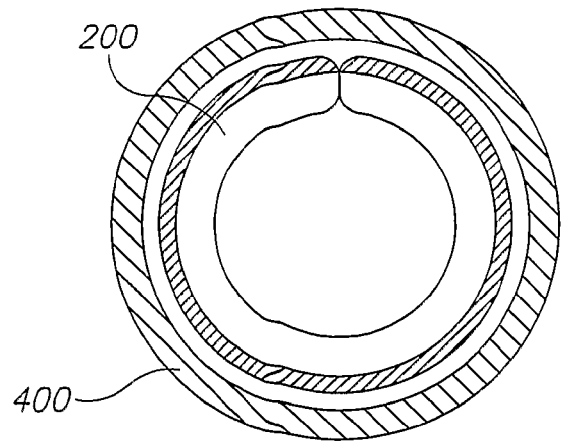
FIG. 5B is cross-sectional cutaway view of the device within the applicator in accordance with an exemplary embodiment of the invention.

FIG. 5A shows a cutaway view of applicator 400 in an exemplary embodiment of the invention. A prolapse treating device 200 is collapsed into a small cross-sectional configuration within applicator 400. Optionally, any of the devices described or suggested herein may be used with the applicator 400. As explained above, device 200 is collapsed to allow for easy and more comfortable insertion into the vagina. FIG. 5B shows a cross-sectional view of applicator 400 in an exemplary embodiment of the invention where the prolapse treatment device 200 is collapsed for storage prior to insertion into the vagina.

Figure 6A:
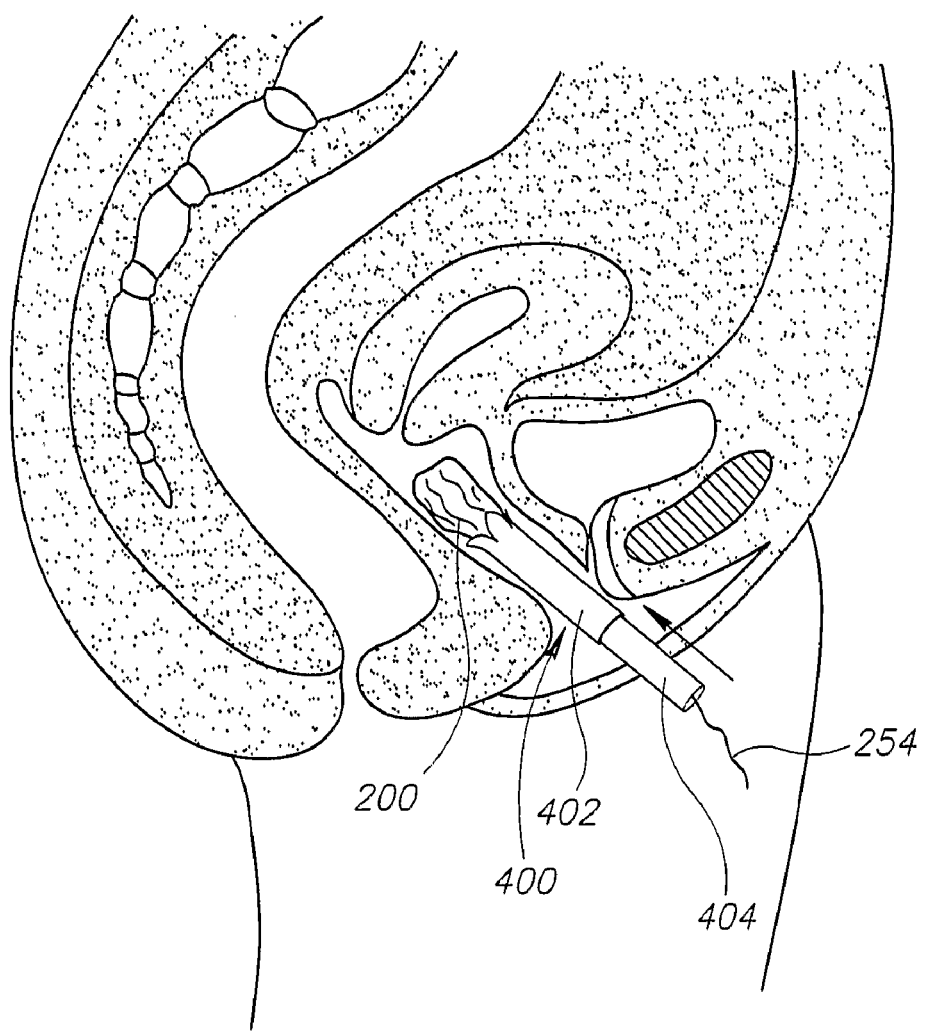
FIG. 6A is a view of the female pelvic region showing a prolapse treatment device being inserted in accordance with an exemplary embodiment of the invention.

Referring to FIG. 6A, applicator 400 is seen being inserted into the vagina for deployment of the prolapse treatment device located within. In an exemplary embodiment of the invention, distal end 402 is inserted first into the vagina. The proximal end 404 portion of applicator 400 is partially pushed towards distal end 402 and some of prolapse device 200 has deployed into the vagina. Continued pushing of proximal end 404 towards distal end 402 will result in device 200 being completely free of the applicator 400. Upon complete deployment of device 200, applicator 400 is removed from the vagina, leaving the device in situ. In an exemplary embodiment of the invention, device displacer 254 stays connected to device 200 throughout. In some embodiments, an applicator is not used to deploy device 200 in the vagina.

Figure 6B:
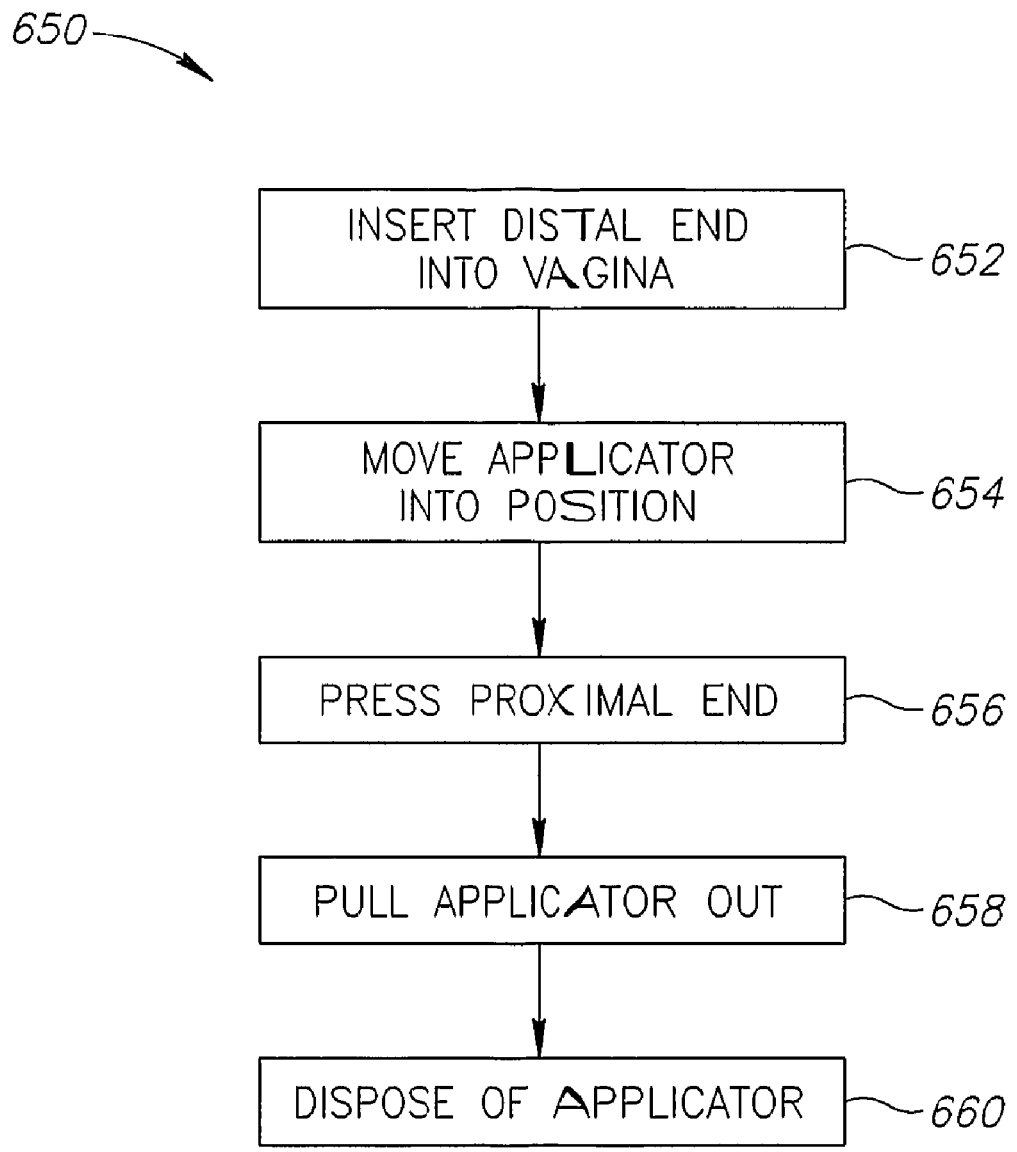
FIG. 6B is a flowchart depicting the insertion process in accordance with an exemplary embodiment of the invention.

A flowchart 650 is depicted in FIG. 6B which describes the process of inserting a prolapse treatment device in accordance with an exemplary embodiment of the invention. Actions 652-660, illustrate a process for insertion of a device according to an exemplary embodiment of the invention which is similar to other processes of insertion described herein.

Figure 6C:
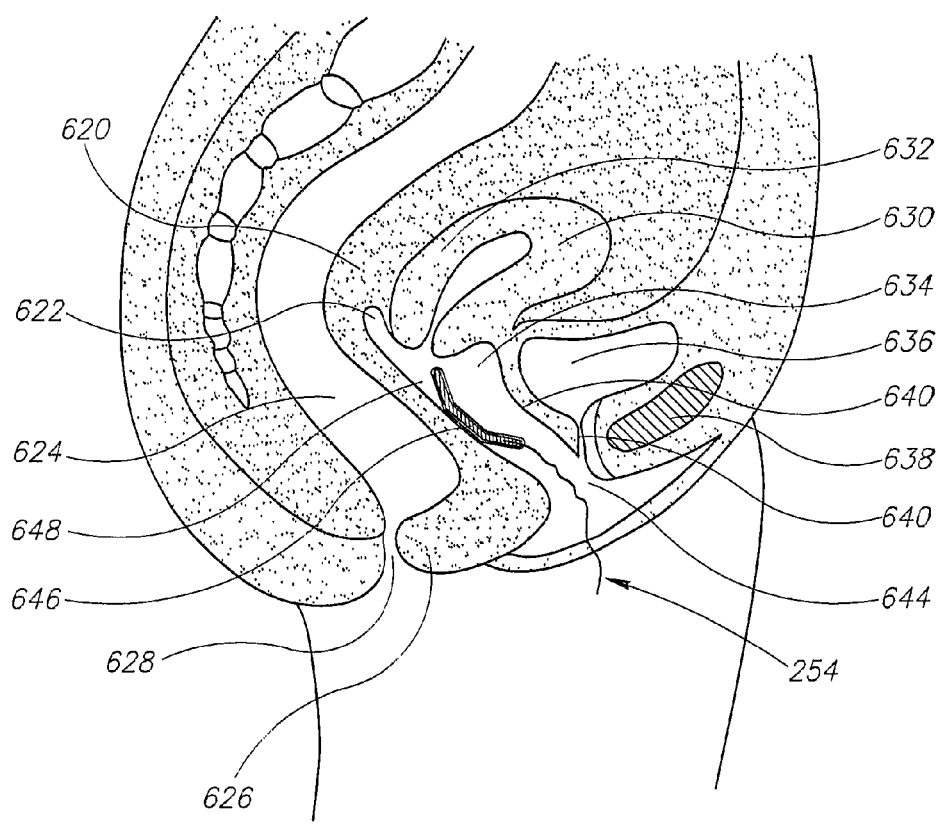
FIG. 6C is an illustration of the female pelvic region showing a prolapse treatment device in situ in accordance with an exemplary embodiment of the invention.

In an exemplary embodiment of the invention, after insertion, the flexible nature of device 200 allows it to gain all, or at least some, of its pre-intended diameter within the vagina, depicted in FIG. 6C. The device anchors itself under the bladder 636 between the uterine cervix 630 and the pubic bone 638. String 254 protrudes out or near the opening of the vaginal introitus 644, as with the regular menstrual tampon, allowing for removal.

Figure 6D:
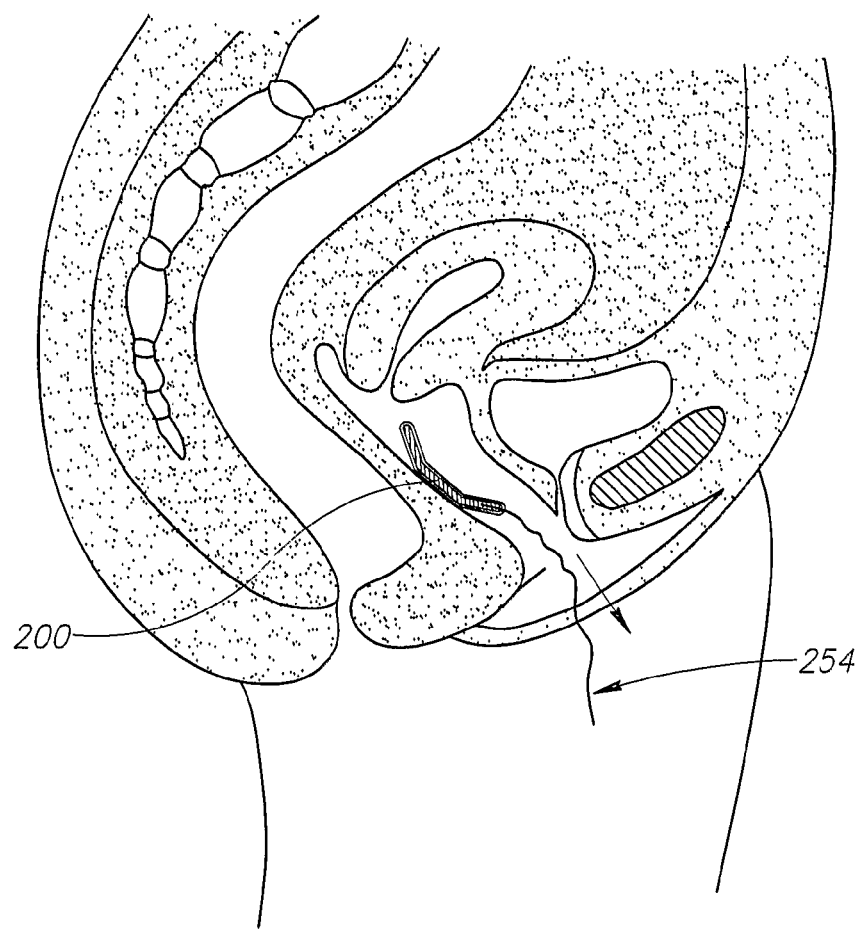
FIG. 6D is a view of the female pelvic region showing a prolapse treatment device being removed in accordance with an exemplary embodiment of the invention.

Referring to FIG. 6D, removal of the device is shown. In some embodiments of the invention, a force applied to device displacer 254 in a direction away from the vaginal opening causes the flexible prolapse device to begin deforming its shape. In an exemplary embodiment of the invention, the device becomes elongated, to form an ovoid shape, with the long axis of the ovoid extending along the vaginal axis. The shape deformation that occurs is sufficient to allow the device to become dislodged and removed comfortably and with ease. Optionally, the device is removed without the use of device displacer 254.

A Disassembling Prolapse Treatment Device

Figure 7A:
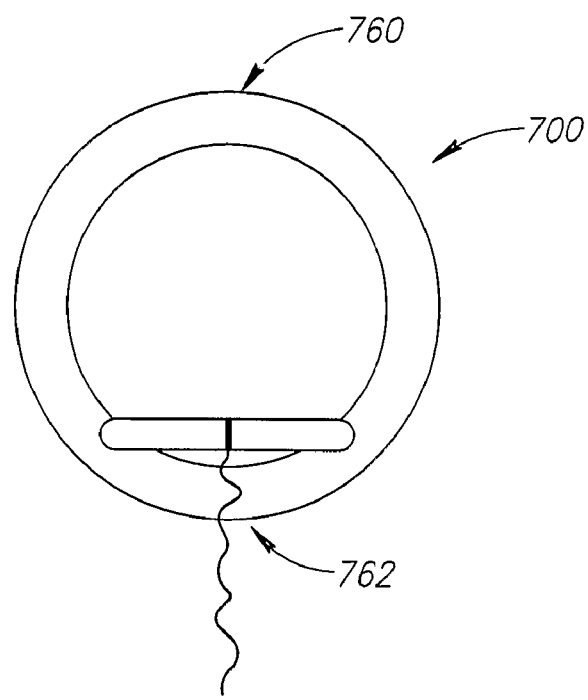
FIG. 7A is a front view of a closed dismantling prolapse treatment device in accordance with an exemplary embodiment of the invention.
Figure 7B:
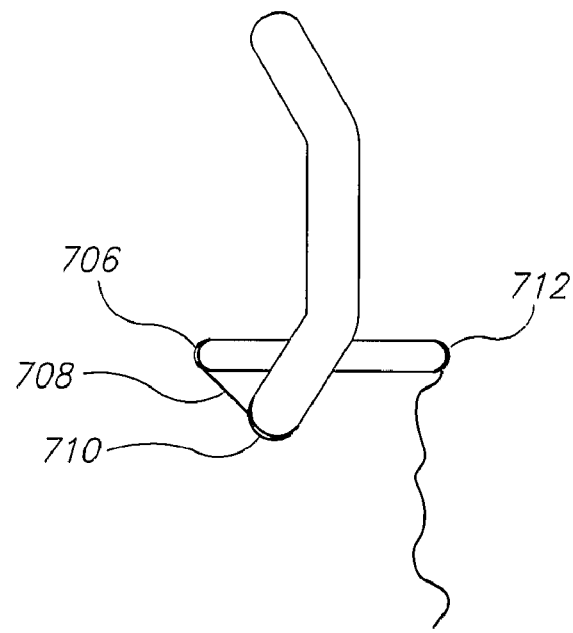
FIG. 7B is a profile view of a closed dismantling prolapse treatment device in accordance with an exemplary embodiment of the invention.
Figure 7C:
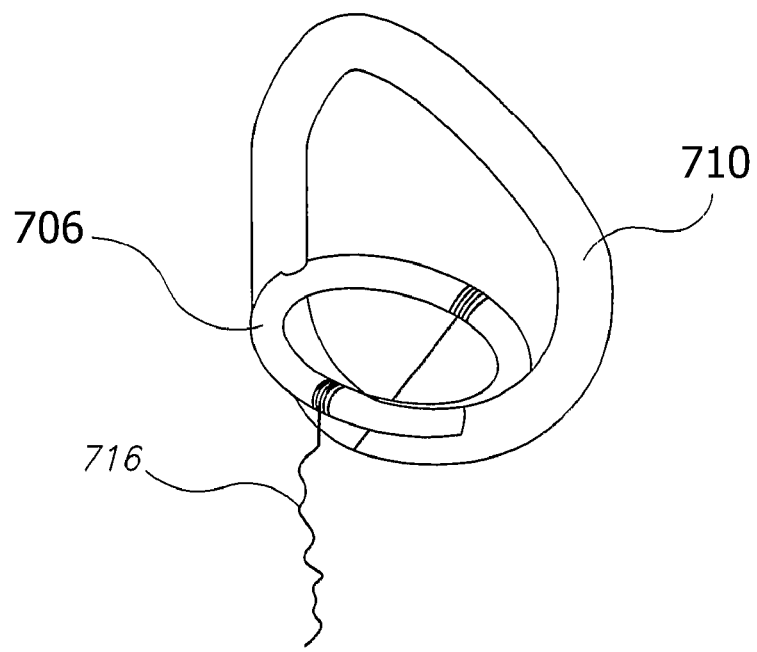
FIG. 7C is a perspective view of a closed dismantling prolapse treatment device in accordance with an exemplary embodiment of the invention.

Turning to FIGS. 7A-C, a closed prolapse device 700 with an anchoring body is depicted, in an exemplary embodiment of the invention. In an exemplary embodiment of the invention, an anchoring body 706 is pre-attached to the main body 710 of device 700. While a ring shape is depicted for main body 710, it should be understood that any shape which is capable of providing stretching to the vaginal walls for support can be used. Such shapes can be ovoid, oblong or multi-sided. In an exemplary embodiment of the invention, device 700 is inserted into the vagina such that a distal end 760 is located substantially opposite the vaginal opening from device 700. Correspondingly, proximal end 762 of device 700 is located nearer to the vaginal opening and device displacer 716. In an exemplary embodiment of the invention, device 700 is inserted such that direct pressure is not exerted on the urethra by device 700. The anchoring body 706 rests within two optionally deformable receiving sites, shown in FIG. 8A, which are small indentations located on the inner circumference of main body 710, in some exemplary embodiments of the invention. Optionally, receiving sites are holes through main body 710.

The two indentations are of sufficient size to hold anchoring body 706 securely but allow the anchoring body to come loose upon the application of removal force. In an exemplary embodiment of the invention, removal force is applied in a direction towards the vaginal opening and away from the uterus. It should be noted that it is likely that the lateral pressure applied by the vaginal wall onto device 700 assists with holding anchoring body 706 in the indentations and does not operate to dislodge anchoring body 706 from main body 710. Alternatively or additionally, anchoring body 706 comes loose from main body 710 upon deformation of the anchoring body when removal force is applied to the anchoring body.

Figure 7D:
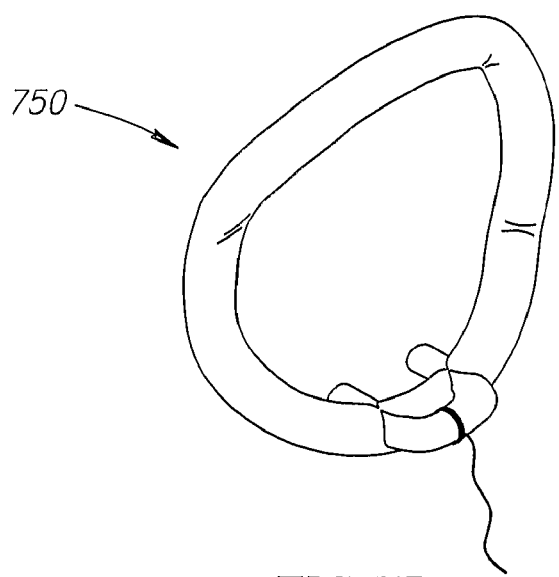
FIG. 7D is a perspective view of a closed dismantling prolapse treatment device in accordance with an exemplary embodiment of the invention.
Figure 7E:
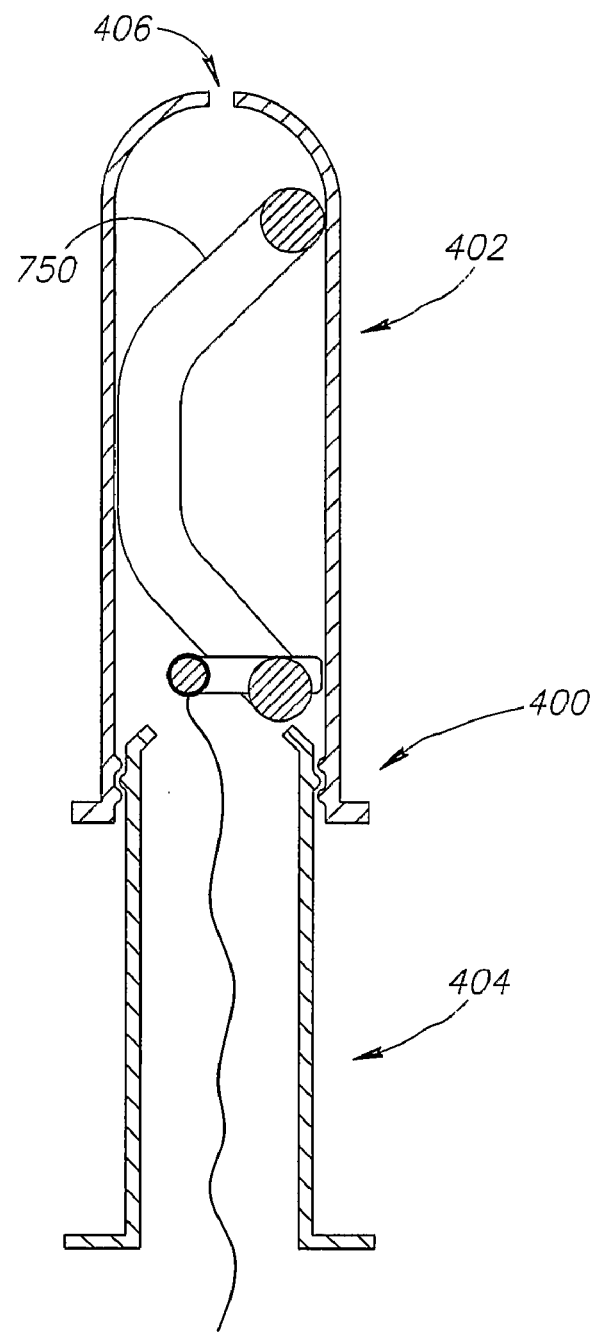
FIG. 7E is a cutaway view of a closed dismantling prolapse treatment device in an applicator prior to deployment in accordance with an exemplary embodiment of the invention.

A device displacer 712 is attached to anchoring body 706. In an exemplary embodiment of the invention, a connecting string 708 statically connects main body 710 and anchoring body 706. Optionally, the anchoring body is flexible. Optionally, the anchoring body is manufactured from a plastic material. In some embodiments of the invention, the anchoring body is larger or smaller than shown in the Figures. Optionally, the indentation sites are located elsewhere on main body 710. As described above, one of the primary concerns with using prolapse treatment devices is their tendency to become unintentionally dislodged, even falling out of the vagina in certain cases. The provision of anchoring body 706 provides a means for combating dislodgment, acting additionally or alternatively to main body 710. It should be understood that any shape which is capable of being removably inserted into main body 710 and which acts to prevent device 700 from becoming unintentionally dislodged can be used. One such embodiment 750 is shown in FIG. 7D, in which a squared horseshoe-shaped body is used as an anchoring body. A cutaway view of an exemplary device, as depicted in FIG. 7D, is shown in FIG. 7E in an exemplary embodiment of an applicator prior to deployment. As with main body 710, such shapes can be ovoid, oblong or multi-sided.

Figure 8A:
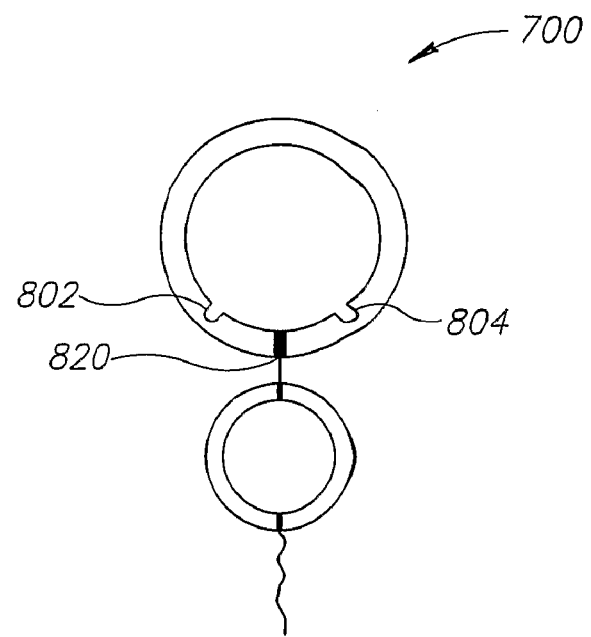
FIG. 8A is a front view of an open dismantling prolapse treatment device in accordance with an exemplary embodiment of the invention.
Figure 8B:
FIG. 8B is a profile view of an open dismantling prolapse treatment device in accordance with an exemplary embodiment of the invention.
Figure 8C:
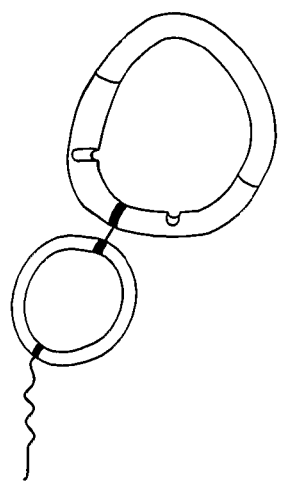
FIG. 8C is a perspective view of an open dismantling prolapse treatment device in accordance with an exemplary embodiment of the invention.

Not only does anchoring body 706 combat unintentional movement of the prolapse device, it is optionally in some embodiments adapted to detach from main ring 710 for an easier and more comfortable removal. FIGS. 8A-C show device 700 in a dismantled state. After device displacer 712 is pulled, anchoring body 706 becomes dislodged from the two indentations 802 and 804 located on the inner circumference of main body 710. However, anchoring body 706 optionally remains connected to main body 710 via connecting string 708. In some embodiments of the invention, anchoring body 706 remains attached to main body 710 but adjusts its relationship to main body 710, thereby altering the configuration of device 700.

Figure 9:
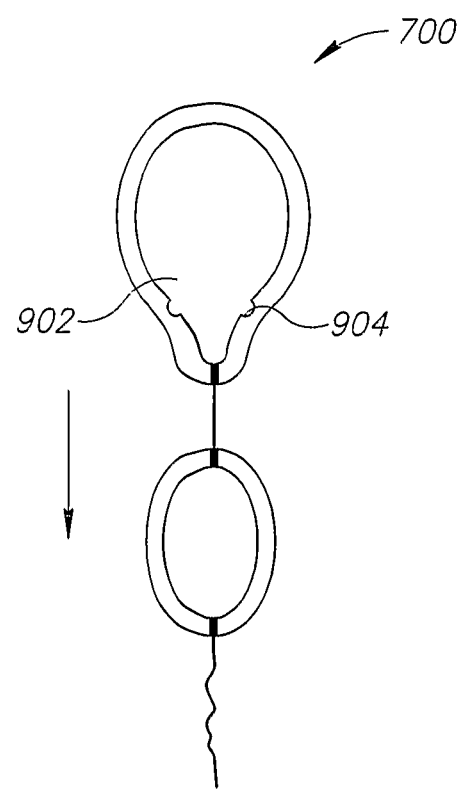
FIG. 9 is a front view of an open dismantling prolapse treatment device which has reduced its profile as a result of an application of removing force in accordance with an exemplary embodiment of the invention.

Referring now to FIG. 9, device 700 is shown at a more advanced stage of removal. In an exemplary embodiment of the invention, indentations 802 and 804 are adapted to give way and collapse main body 710 upon the exertion of a predetermined removal force on device displacer 712. The indentations 902 and 904 begin to deform as a result of having a lower strength than the rest of device 700. It is important to note however, that in some embodiments at least one indentation is not so weak as to completely break, leaving a portion of device 700 still within the vagina. As the indentations begin to give way, device 700 begins to deform to form a more elongated shape. The elongated shape has a longer axis in line with the longer vaginal axis. This deformation essentially reduces the profile size of device 700, allowing for easier and more comfortable removal. In an exemplary embodiment where main body 710 is comprised of a single material, indentations 902 and 904 deform as a result of being the weakest section of main body 710.

In an exemplary embodiment of the invention, main body 710 is rigid with flexible springs interconnecting arc portions thereof. The springs allow main body 710 to elongate under a removal force, reducing the profile of device 700 and allowing for easier, more comfortable removal. Additionally or alternatively, indentations 902 and 904 are hinged.

In an exemplary embodiment of the invention, an assembled prolapse treatment device including the anchoring body is inserted into the vagina with an applicator. The device is intended to be applied into the vagina with an applicator much like the insertion of a regular menstrual tampon. That is, application of pressure towards distal end 402 using proximal end 404 like a plunger, exit 406 opens and the prolapse treating device 200 located within exits applicator 400 and deploys in the vagina. After insertion, the device should expand significantly to the predefined shape and size, thereby exerting predefined appropriate pressure on both lateral vaginal walls, pushing them aside. The apex of the vagina is pushed upwards at the same time due to the increased tension of the vaginal walls. Expansion of the device eventually creates linear stretching of the anterior and posterior vaginal walls, while creating a new shape of intra-vaginal hollow. Optionally, the device is inserted without the use of an applicator.

An Adjustable Rigidity Prolapse Treatment Device

Figure 10A:
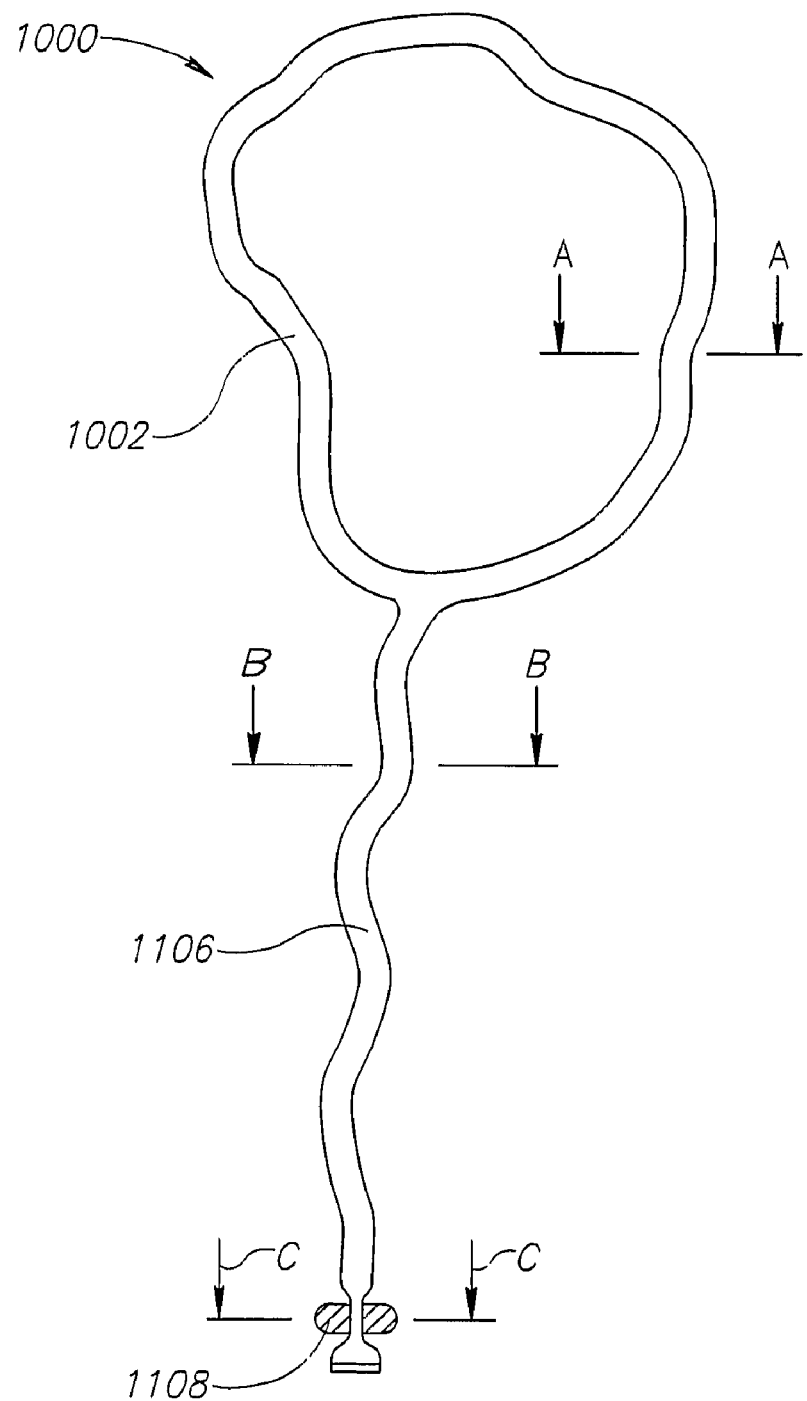
FIG. 10A is a view of an embodiment of a prolapse treatment device in a flaccid configuration in accordance with an exemplary embodiment of the invention.
Figure 10B:
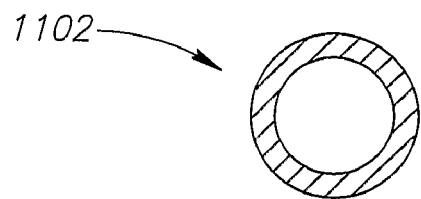
FIG. 10B is a cross-sectional view of the device along line A-A of FIG. 10A in accordance with an exemplary embodiment of the invention.
Figure 10C:
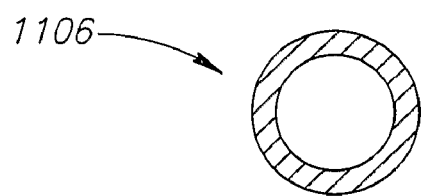
FIG. 10C is a cross-sectional view of the device along line B-B of FIG. 10A in accordance with an exemplary embodiment of the invention.

FIG. 10A illustrates an embodiment of a prolapse treatment device 1000 in a flaccid condition. In an exemplary embodiment of the invention, the main body 1102 of the device is a flexible hollow circular body. Optionally, the main body is another closed shape such as elliptical, ovoid, or multi-sided. In an exemplary embodiment of the invention, main body 1102 is filled with biocompatible, non-compressible fluid. Optionally, the biocompatible, non-compressible fluid is water-based. In an exemplary embodiment of the invention, main body 1102 has an attached hollow tube 1106. The lumen of main body 1102, shown in FIG. 10B, and of hollow tube 1106, shown in FIG. 10C, are in fluid communication, that is, they have a continuous hollow space. The lumen of hollow tube 1106 is therefore also filled with the biocompatible, non-compressible fluid.

Figure 10D:
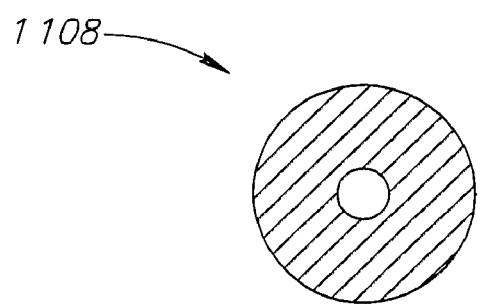
FIG. 10D is a cross-sectional view of the device along line C-C of FIG. 10A in accordance with an exemplary embodiment of the invention.

In an exemplary embodiment of the invention, hollow tube 1106 has at least two basic functions. First, it serves as a reservoir for the fluid outside main body 1102. A fluid blocking mechanism 1108 is provided around hollow tube 1106 which has a small inside diameter in relation to the diameter of hollow tube 1106, shown in FIG. 10D. Optionally, the fluid blocking mechanism 1108 is a ring. Optionally, the fluid blocking mechanism 1108 is a bead. The fluid blocking mechanism 1108 is attached around hollow tube 1106 so that none of the fluid located inside tube 1106 can escape through the tube where it is compressed by blocking mechanism 1108. Furthermore, blocking mechanism 1108 compresses the lumen of the tube sufficiently to prevent fluid from escaping when the blocking mechanism is moved up hollow tube 1106 towards main body 1102. It can be seen from the Figure that shifting blocking mechanism 1108 up and down hollow tube 1106 shifts the fluid in and out of main body 1102. Optionally, main body 1102 and tube 1106 may be made of a flexible material. Optionally, the flexible material is silicone or polyurethane. In some embodiments of the invention, main body 1102 and hollow tube 1106 are not made of the same material.

A second use for the hollow tube 1106 in an exemplary embodiment of the invention is its use as a means for removal of device 1000 from the vagina. As described in other embodiments of prolapse treatment devices, a device displacer is provided, such as a string, which the user can pull in order to remove the device from the vagina. In the same fashion, the user can remove device 1000 from the vagina by pulling on hollow tube 1106. Removal of device 1000 can be obtained in this manner irrespective of whether the device is in a flaccid or turgid condition. In some exemplary embodiments of the invention, pulling on hollow tube 1106 causes some elastic deformation of tube 1106 which increases the volume available for the fluid located within device 1000 to flow into tube 1106. As a result, fluid may flow from main body 1002 and into tube 1106 causing at least a slight collapse of the main body, and thus, allowing for easier removal.

Figure 11:
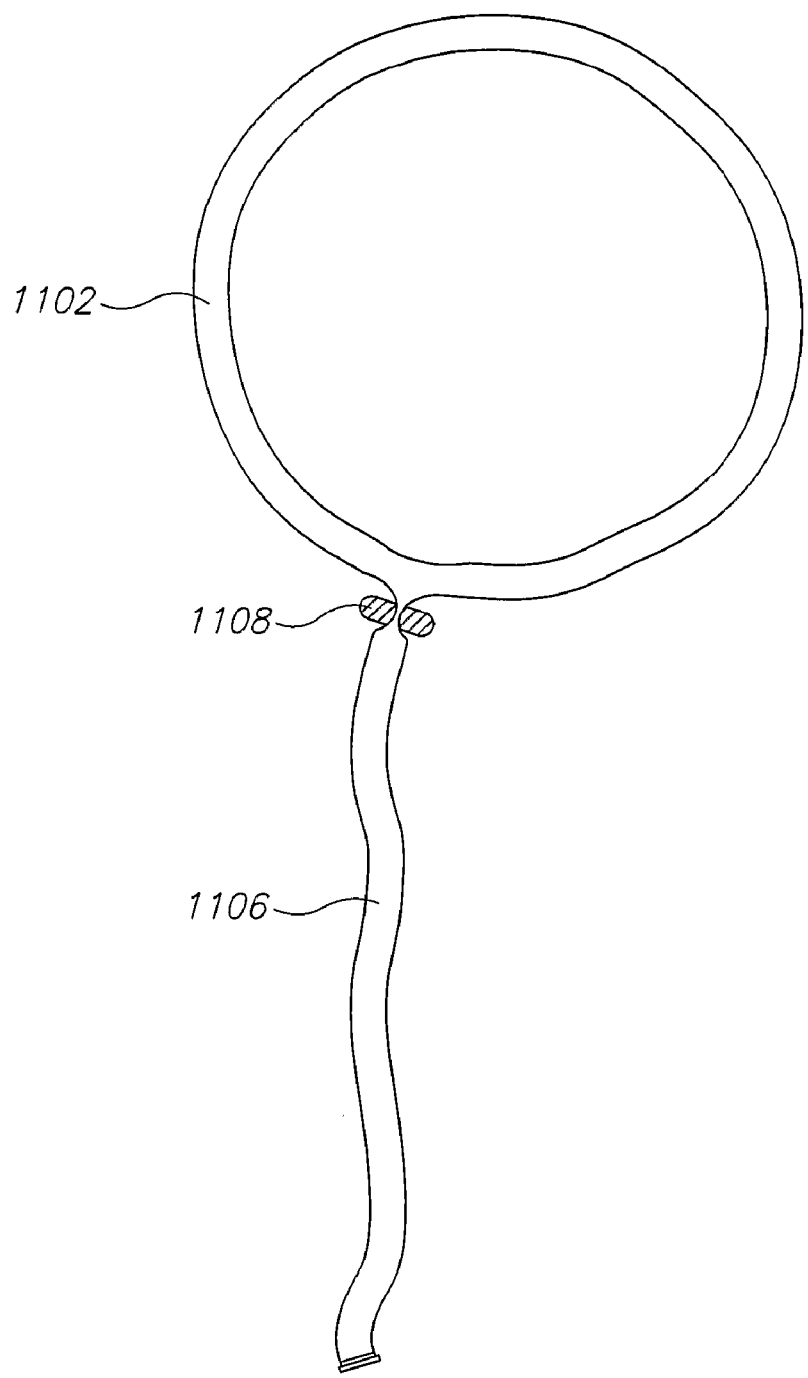
FIG. 11 is a view of an embodiment of a prolapse treatment device in a turgid configuration in accordance with an exemplary embodiment of the invention; and, FIG. 12 is a cutaway view of an embodiment of a prolapse treatment device positioned in an applicator in accordance with an exemplary embodiment of the invention.

Referring to FIG. 11, a turgid prolapse treatment device 1000 in accordance with an exemplary embodiment of the invention is shown. In a flaccid form of main body 1102, blocking mechanism 1108 is away from main body 1102 at the far end of tube 1106, thereby allowing for fluid to accumulate within tube 1106, as shown in FIG. 10A. In such a configuration, there is now low fluid pressure within main body 1102. When blocking mechanism 1108 is moved towards main body 1102, blocking mechanism 1108 squeezes the fluid from tube 1106 into main body 1102, as a result of decreasing available volume for the fluid in tube 1106. The main body 1102 is adjusted by increasing its rigidity to a level sufficient for treating prolapse in the individual patient. The increased rigidity of the device 1000 exerts high pressure on the walls of the vagina, thereby pushing them aside and correcting the prolapse.

Figure 12:
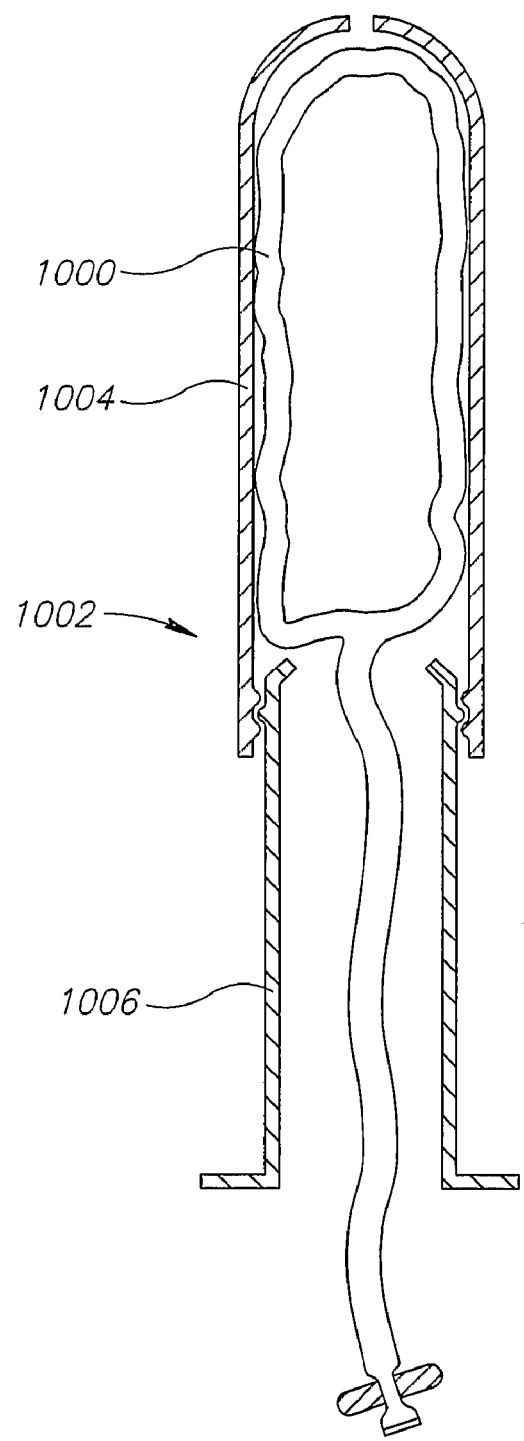

Referring now to FIG. 12, a cutaway view of an embodiment of a prolapse treatment device 1000 is shown positioned within an applicator 1002. In an embodiment of the invention, the applicator comprises a distal end 1004 and a proximal end 1006. In addition, distal end 1004 is provided with an exit 1008, which is used for allowing device 1000 out of applicator 1002 and into position for prolapse treatment. The device 1000 is moved out of applicator 1002 by exerting pressure towards distal end 1004 on proximal end 1006 while holding distal end 1004 substantially in place. The proximal end 1006 acts like a plunger, pushing device 1000 out of exit 1008 located at distal end 1004. Once device 1000 is in position to treat prolapse, the applicator 1002 is removed from the vagina, and optionally disposed of.

Figure 13:
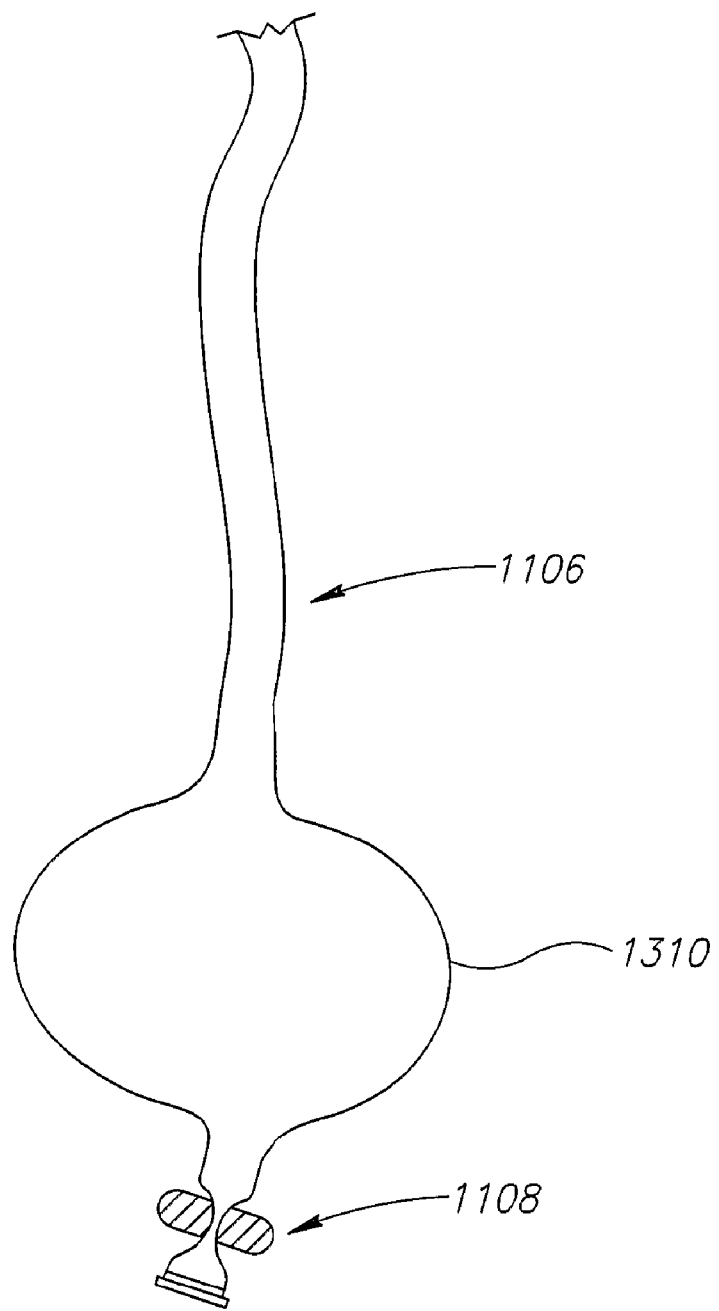
FIG. 13 is an illustration of an embodiment of a prolapse treatment device with a fluid reservoir in accordance with an exemplary embodiment of the invention.

It can be seen from FIGS. 10A-D and 11 that the amount of fluid that can be pushed into the main body 1102 is limited by the volume of the hollow tube 1106. In certain cases, it may be desirable to enhance the volume of the fluid available in the tube 1106. Therefore, in an embodiment of the invention, additional reservoir space 1310 is provided in the hollow tube 1106. FIG. 13 illustrates a hollow tube 1106 which has been enhanced by providing it with additional fluid reservoir space 1310. The extra fluid contained in additional reservoir space 1310 can be used to obtain increased rigidity of the main body assuming the same length of hollow tube. Alternatively or additionally, use of additional reservoir space 1310 allows the hollow tube 1106 to be shortened and yet provide the same amount of fluid to the main body 1102.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of features noted in the described embodiments will occur to persons of the art. When used in the following claims, the terms "comprises", "includes", "have" and their conjugates mean "including but not limited to". The scope of the invention is limited only by the following claims.

The invention claimed is:

1. An apparatus for treating pelvic organ prolapse, comprising:
   a main body adapted to provide pelvic organ support when inserted into a vagina; and,
   an anchoring body, wherein said anchoring body selectively rests within at least one receiving site located on the main body allowing the anchoring body to be attached to the main body when resting within the at least one receiving site and removed from the main body when detached from the at least one receiving site;
   wherein the main body is a ring shaped main body sized and shaped to apply appropriate pressure on lateral vaginal walls for treating pelvic organ prolapse,
   characterized in that the ring shaped main body is flexible, the device being foldable at least three different points or along at least two axes, such that insertion of the main body does not have to be precise and that the ring shaped main body naturally settles into the appropriate rotational position for prolapse treatment taking a pre-defined multi-planar shape; and further comprising,
   an applicator enclosing the ring shaped main body for inserting said ring shaped main body into a vagina.

2. An apparatus according to claim 1 wherein said multi-planar main body extends in three axes.

3. An apparatus according to claim 1 further comprising a device displacer.

4. An apparatus according to claim 1 further comprising a soft external layer located on at least a portion of said main body, said soft external layer adapted to enhance comfort.

5. An apparatus according to claim 4 wherein the soft external layer is comprised of sponge rubber.

6. An apparatus according to claim 1 further comprising a soft external layer located on at least a portion of said main body, said soft external layer adapted to prevent necrosis.

7. An apparatus according to claim 1 wherein said apparatus is at least partially flexible, said apparatus flexible in response to forces applied to it while in the vagina and during removal.

8. An apparatus according to claim 1 which is disposable.

9. An apparatus according to claim 1 wherein said main body is adapted to not directly compress a urethra after insertion.

10. An apparatus according to claim 1 wherein the ring shaped main body is provided with a varying degree of stiffness along its length enabling the main body to assume the predefined multi-planar shape upon insertion.

11. An apparatus according to claim 1 wherein the ring shaped main body elastically expands into the predefined multi-planar shape upon insertion.

12. An apparatus for treating pelvic organ prolapse, comprising:
   a main body adapted to provide pelvic organ support when inserted into a vagina; and,
   an anchoring body, wherein said anchoring body selectively rests within at least one receiving site located on the main body allowing the anchoring body to be attached to the main body when resting within the at least one receiving site and removed from the main body when detached from the at least one receiving site wherein said anchoring body is selected from a group consisting of ring shaped, ovoid and multi-sided.

13. An apparatus according to claim 12 wherein said main body is non-planar, extending along three axes.

14. An apparatus according to claim 12 further comprising a device displacer.

15. An apparatus according to claim 12 further comprising a soft external layer located on at least a portion of said main body.

16. An apparatus according to claim 12 wherein said apparatus is adapted to be flexible in response to force applied on said apparatus while in said vagina and during removal from said vagina.

17. An apparatus according to claim 12 which is disposable.

18. An apparatus according to claim 12 wherein said main body is deformable upon the application of a removal force towards an opening of said vagina.

19. An apparatus according to claim 12 further comprising an applicator adapted for insertion of said apparatus.

20. An apparatus according to claim 12, wherein the main body is a thin main body adapted to provide pelvic organ support when inserted into a vagina, which main body is deformable at least three points thereon.

21. An apparatus according to claim 20 wherein said main body is non-planar, extending along three axes.

22. An apparatus according to claim 20 further comprising a device displacer adapted to impart movement to said apparatus.

23. An apparatus according to claim 20 further comprising a soft external layer located on at least a portion of said main body, said soft external layer adapted to prevent necrosis.

24. An apparatus according to claim 20 wherein said apparatus is adapted to be flexible in response to force applied on said apparatus while in said vagina and during removal from said vagina.

25. An apparatus according to claim 20 which is disposable.

26. An apparatus according to claim 12, wherein the at least one receiving site is deformable.

27. An apparatus according to claim 12, wherein the at least one receiving site is a hole through the main body.

28. An apparatus according to claim 12, wherein the at least one receiving site is an indentation on the main body.

29. An apparatus according to claim 12, wherein the at least one receiving site is located on the inner circumference of the main body.

30. An apparatus for treating pelvic organ prolapse, comprising:

a main body adapted to provide pelvic organ support when inserted into a vagina; and, an anchoring body, wherein said anchoring body selectively rests within at least one receiving site located on the main body allowing the anchoring body to be attached to the main body when resting within the at least one receiving site and removed from the main body when detached from the at least one receiving site;

wherein the main body is a thin main body adapted to provide pelvic organ support when inserted into a vagina, which main body is deformable at least three points thereon and wherein said apparatus does not directly compress a urethra upon insertion.

31. A method of treating pelvic organ prolapse, comprising:

inserting into a vagina an apparatus comprising a first main body portion and a second anchoring portion for treating pelvic organ prolapse;

positioning said apparatus within said vagina wherein said apparatus exhibits a non-planar configuration after said insertion, wherein said positioning does not apply direct pressure to a urethra;

anchoring the apparatus within the vagina using the second anchoring portion; and, removing said apparatus from said vagina by removing the second anchoring portion from at least one receiving site on the first main body portion to reduce the profile of the apparatus.

32. A method according to claim 31 wherein inserting is facilitated by using an applicator.

33. A method according to claim 31 wherein said removing is facilitated by a device displacer adapted to impart movement to said apparatus.

34. A method according to claim 31 further comprising disposing of said apparatus.

* * * * *